(12) United States Patent
Kikelj et al.

(10) Patent No.: US 7,112,590 B2
(45) Date of Patent: Sep. 26, 2006

(54) THROMBIN INHIBITORS

(75) Inventors: Danijel Kikelj, Ljubljana (SI); Lucija Peterlin, Medvode (SI); Petra Marinko, Ljubljana (SI); Matej Breznik, Ljubljana (SI); Mojca Stregnar, Ljubljana (SI); Bakija Alenka Trampuz, Ljubljana (SI); Marjana Fortuna, Grosuplje (SI)

(73) Assignees: LEK Pharmaceuticals d.d., Ljubljana (SI); University of Ljubljana, Faculty of Pharmacy, Ljubljana (SI)

( * ) Notice: Subject to any disclaimer, the term of this patent is extended or adjusted under 35 U.S.C. 154(b) by 289 days.

(21) Appl. No.: 10/275,215

(22) PCT Filed: May 4, 2001

(86) PCT No.: PCT/GB01/01997

§ 371 (c)(1), (2), (4) Date: Jan. 31, 2003

(87) PCT Pub. No.: WO01/85760

PCT Pub. Date: Nov. 15, 2001

(65) Prior Publication Data
US 2003/0191139 A1 Oct. 9, 2003

(30) Foreign Application Priority Data
May 5, 2000 (SI) .............................. P-200000111

(51) Int. Cl.
*C07D 487/02* (2006.01)
*C07D 498/02* (2006.01)
*C07D 491/02* (2006.01)
*A61K 31/4745* (2006.01)

(52) U.S. Cl. .............................. 514/258.1; 514/264.1; 514/266.22; 514/266.23; 514/300; 514/301; 514/302; 514/115; 544/279; 544/284; 546/114; 548/152; 548/217; 548/304.7; 548/360.1

(58) Field of Classification Search ............. 514/258.1, 514/264.1, 266.22, 266.23, 300, 301, 302, 514/115, 119; 544/279, 284; 548/152, 217, 548/304, 360.1
See application file for complete search history.

(56) References Cited

U.S. PATENT DOCUMENTS

| | | | |
|---|---|---|---|
| 5,510,369 A | 4/1996 | Lumma et al. | 514/422 |
| 5,523,308 A | 6/1996 | Costanzo et al. | 514/317 |
| 5,811,402 A | 9/1998 | Klimkowski et al. | 514/19 |
| 5,827,866 A | 10/1998 | Costanzo et al. | 514/369 |

FOREIGN PATENT DOCUMENTS

WO   WO 98/47876   10/1998

OTHER PUBLICATIONS

Das J et al. "Thrombin Active Site Inhibitors", Bioorganic & Medicinal Chemistry, GB, Elsevier Science Ltd, vol. 3, No. 8, 1995, pp. 999-1007, XP000995766.
International Search Report, Jul. 9, 2001.

*Primary Examiner*—Shaojia A. Jiang
*Assistant Examiner*—Ganapathy Krishnan
(74) *Attorney, Agent, or Firm*—Bromberg & Sunstein LLP

(57) ABSTRACT

The invention relates to compounds that are heterocyclic derivatives of dipeptides and dipeptides mimetics and pharmaceutically acceptable salts thereof. The compounds are used as thrombin inhibitors

14 Claims, No Drawings

THROMBIN INHIBITORS

TECHNICAL FIELD

The invention belongs to the field of pharmaceutical industry and relates to novel heterocyclic derivatives of dipeptides and dipeptide mimetics in the form of a mixture of diastereomers and in the form of pure diastereomers, methods for their preparation and pharmaceutical compositions containing them. Novel heterocyclic derivatives of dipeptides and dipeptide mimetics are inhibitors of thrombin and other serine proteases which may play a role in blood coagulation and which may have the anticoagulant activity in mammals.

TECHNICAL PROBLEM

Heparins and coumarins which are predominantly used for inhibition of coagulation in vivo, have a number of untoward and unexpected effects. Heparin is used parenterally and acts by potentiating the inhibitory effect of the physiological thrombin inhibitor endogenous antithrombin III. Since an amount of antithrombin III in plasma may greatly vary and inhibition of bound thrombin is not feasible via the described indirect mechanism. Treatment with heparins may be ineffective. Heparins have poor bioavailability and a narrow therapeutic range. Coumarins inhibit thrombin synthesis by blocking γ-carboxylation of glutamate in the synthesis of prothrombin and factors VII, IX and X. Therefore the effect may be delayed for a few days. Treatment with coumarins should be regularly monitored by coagulation tests. Due to the disadvantages of heparin and coumarins in anticoagulant therapy, there is a need for new substances with rapid onset of anticoagulant effect independent of antithrombin III and which may also be effective in oral administration. Low molecular weight thrombin inhibitors appear to be of growing importance in this area.

PRIOR ART

Serine protease thrombin is a key enzyme in the processes of blood coagulation and thus in the development of thrombosis. Its principal action is to convert soluble fibrinogen into insoluble fibrin which forms a mechanical matrix for the developing clot. In addition, it mechanically strengthens the clot by activating factor XIII which covalently links fibrin monomers and stimulates platelet aggregation. By a positive feedback mechanism via activation of factors V and VIII the thrombin concentration at the site of injury is increased. With the above role played in hemostasis, thrombin has become a target molecule in the search of new anticoagulants (Sanderson P. E. J., Naylor-Olsen A. M. Curr. Med. Chem. 1998, 5, 289–304.; Menear K. Curr. Med. Chem. 1998, 5, 457–468.; Breznik M., Peèar S. Farm. vestn. 1997, 48, 545–560; Sanderson P. E. J. Med. Res. Rev. 1999, 19, 179–197).

The active site of thrombin with the characteristic catalytic triad (Asp 189, His 57, Ser 195) can be divided into three binding areas: the S1 pocket giving the enzyme specificity for the basic part of the inhibitor molecule (P1), S2 hydrophobic area which prevents access of the inhibitors and the substrate to the active site and a larger S3 hydrophobic area (Bode W., Mayr I., Baumann U. et al. The EMBO Journal 1998, 8, 3467–3475).

Based on knowledge of the crystalline structure of thrombin, a number of low molecular weight inhibitors have now been developed which act at the thrombin active site. An ideal thrombin inhibitor should have good bioavailability, long half-life and be suitable for oral administration. Achievement of these aims is limited either by a basic guanidine or amidine group, present in many known thrombin inhibitors or by a reactive electrophilic group, present in electrophilic thrombin inhibitors, for example, efegatran, PPACK. An important criterion in designing thrombin inhibitors is also the selectivity to other serine proteases, such as trypsin, factor Xa, urokinase, tissue plasminogen activator and plasmin (Kimball S. D. Current Pharmaceutical Design 1995, 1, 441–468.; Das J., Kimball S. D. Bioorg. Med. Chem. 1995, 3, 999–1007).

Low molecular weight inhibitors of the thrombin active site mimic a tripeptide sequence D-Phe-Pro-Arg of natural fibrinogen substrate. The first phase in the development are irreversible inhibitors which covalently react with Ser 195 at the active site. PPACK is a prototype of this type of inhibitor. Despite the fact that inhibitors of this type are very effective, due to high reactivity they are potentially toxic and of low selectivity, and their use is disputable. Argatroban is the first highly effective and selective reversible inhibitor available on the market in Japan and the USA (Novastan® and Slonnon®). In Europe it is in the phase of clinical testing. A large number of structurally different, active reversible inhibitors with hydrophilic basic groups having low bioavailability after oral administration have been synthesized to date (Menear K. Curr. Med. Chem. 1998, 5, 457–468).

By extensive modification of the P1 part of thrombin inhibitors, primarily by substituting basic guanidine or amidine groups with neutral or weakly basic groups, their bioavailability can be increased. Larger groups in this part of the molecule lead to higher selectivity of the inhibitors for thrombin as, compared to the majority of other serine proteases, thrombin has relatively large S1 pocket. Selectivity of thrombin inhibitors is generally estimated regarding their ability for inhibition of trypsin which by form and size of the active site is most closely related to thrombin and has a smaller S1 pocket. Modification of other parts of the molecule (P2 and P3), especially substitution of the ester and amide bonds may additionally increase the stability of thrombin inhibitors in the body. Such thrombin inhibitors are less sensitive to nonspecific proteases and hydrolysis and consequently their half-life increases. (Menear K. Curr. Med. Chem. 1998, 5, 457–468.; Tucker T. J., Brady S. F., Lumma W. C. et al. J. Med. Chem. 1998, 41, 3210–3219).

DESCRIPTION

The invention relates to novel compounds of the general formula (I)

$$D-CO—B-A-Het \qquad (I)$$

in which

| Het is selected from: | | |
|---|---|---|
| Group | | |
| (structure with R¹, R², n = 0,1) | (1.1) | (substituted 6,7-dihydro-5H-cyclopenta[d]pyrimidine, attached to group A via the position 5, 6 or 7 or substituted 5,6,7,8-tetrahydroquinazoline attached to group A via the position 5, 6, 7 or 8), |
| (structure with R¹, R²) | (1.2) | (substituted quinazoline, attached to group A via the position 6), |
| (structure with R¹, R²) | (1.3) | (substituted quinazoline, attached to group A via the position 7), |
| (structure with X, R¹, n = 0, 1) wherein X is S, NH or O | (1.4) | (substituted 1,4,5,6-tetrahydrocyclopenta[d]-imidazole, 5,6-dihydro-4H-cyclopenta[d][1,3]-thiazole, 5,6-dihydro-4H-cyclopenta[d][1,3]-oxazole, attached to group A via the position 4, 5 or 6 or substituted 4,5,6,7-tetrahydro-1,3-benzothiazole, 4,5,6,7-tetrahydro-1H-benzimidazole, 4,5,6,7-tetrahydro-1,3-benzoxazole, attached to group A via the position 4, 5, 6 or 7), |
| (structure with S, R¹) | (1.5) | (substituted 1,3-benzothiazole attached to group A via the position 6), |
| (structure with Y, NH, n = 0, 1) wherein Y is N or CH | (1.6) | (substituted 2,4,5,6-tetrahydrocyclopenta[c]pyrrole, 2,4,5,6-tetrahydrocyclopenta[c]pyrazole, attached to group A via the position 4, 5 or 6 or substituted 4,5,6,7-tetrahydro-2H-indazole 4,5,6,7-tetrahydro-2H-isoindole, attached to group A via the position 4, 5, 6 or 7), |
| (structure with R¹, R²) | (1.7) | (substituted 5,6,7,8-tetrahydropyrido[4,3-d]pyrimidine attached to group A via the position 6), |
| (structure with X, R¹) wherein X is NH, O or S | (1.8) | (substituted 4,5,6,7-tetrahydro-1H-imidazo[4,5-c]pyridine, 4,5,6,7-tetrahydro[1,3]oxazolo[4,5-c]pyiridine, 4,5,6,7-tetrahydro[1,3]thiazolo[4,5-c]pyridine, attached to group A via the position 5), |

-continued

Het is selected from:

| Group | |
|---|---|
| 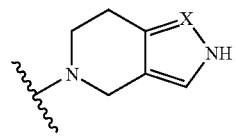 | (1.9) (substituted 4,5,6,7-tetrahydro-2H-pyrazolo[4,3-c]pyridine, 4,5,6,7-tetrahydro-2H-pyrrolo[3,4-c]pyridine, attached to group A via the position 5). |
| wherein Y is N or CH | |
| 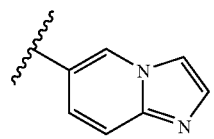 | (1.10) (imidazo[1,2-a]pyridine attached to group A via the position 6). |
| $R^1$ is selected from H and $NH_2$ and $R^2$ is selected from H and $NH_2$, | |

A:
-group —CONH— or —CH$_2$NH— attached to Het by the NH fragment,
-group —CONHCH$_2$— or —CH$_2$NHCH$_2$ attached to Het by the CH$_2$ fragment, group —CH$_2$NHCONH—, —CH$_2$NHCH$_2$CONH— or —CH$_2$NHCOCH$_2$NH— attached to Het by the NH fragment, group —CH$_2$NHCONHCH$_2$—, —CH$_2$NHCH$_2$CONHCH$_2$—, or —CH$_2$NHCOCH$_2$NHCH$_2$—attached to HET by the CH$_2$ fragment, B is selected from the following structures:

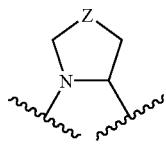 (2.1)

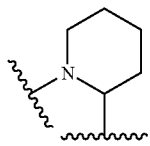 (2.2)

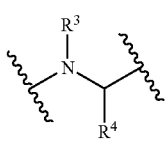 (2.3)

wherein:
Z is CH$_2$, S or CH—OH
$R^3$ is H, straight or branched C$_1$–C$_4$ alkyl, C$_3$–C$_7$ cycloalkyl
$R^4$ is H, straight or branched C$_1$–C$_4$ alkyl, C$_3$–C$_7$ cycloalkyl
In preferred compounds (2.1) Z is CH$_2$.
D is of the general structure:

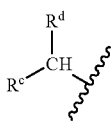 (3.0)

wherein $R^d$ is H, CH$_2$OH, CH$_2$SH or a group

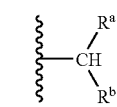 (3.0.1)

wherein
$R^a$ and $R^b$ are independently selected from the following groups:
H,
C$_1$–C$_4$ straight or branched alkyl which can be substituted with C$_3$–C$_7$ cycloalkyl or with 1 to 9 atoms of halogen selected from F, Cl, Br, I,
C$_3$–C$_7$ cycloalkyl,
C$_9$–C$_{10}$ bicycloalkyl,
a stable saturated or unsaturated 5- to 7-membrered monocyclic heterocyclic ring, or a 8- to 10-membrered bicyclic heterocyclic ring which, in addition to carbon atoms, contains 1 to 3 heteroatoms selected from N, O and S in which N or S can be oxidized or N quaternized,
aryl (e.g., phenyl, naphthyl) which can be unsubstituted or optionally substituted at any position with one or two substituents selected from C$_{1-4}$ alkyl, C$_{1-4}$ alkoxy, halogen or hydroxy. Preferred compounds $R^a$ may be phenyl, dichlorophenyl e.g. 3,4-dichlorophenyl or cyclohexyl and $R^b$ may be H. Alternatively $R^a$ and $R^b$ may be independently phenyl or cyclohexyl.
In preferred compounds $R^d$ may be a group 3.0.1.
$R^c$ is selected from the groups:
NH$_2$
NH(CH$_2$)$_n$CH$_3$, where n is 0, 1, 2 or 3,
NH(CH$_2$)$_m$OH, where m is 2, 3 or 4,
NH(CH$_2$)$_k$COOH, where k is 1, 2 or 3,
NH(CH$_2$)$_n$COOR$^5$, where n is 0, 1, 2 or 3 and $R^5$ represents C$_{1-4}$ straight or branched alkyl,
NH(CH$_2$)$_k$CONR$^6$R$^7$, where k is 1, 2 or 3 and $R^6$ in $R^7$ are independently H or straight or branched C$_{1-4}$ alkyl, or $R^6$ and $R^7$ together are —(CH$_2$)$_{4-5}$—, —(CH$_2$)$_2$O (CH$_2$)$_2$— or —(CH$_2$)$_2$NH(CH$_2$)$_2$—, NHO$_2$S(CH$_2$)$_n$—W wherein n is 0, 1, 2 or 3, W represents phenyl, naphthyl, a saturated or unsaturated monocyclic 5- or 6-membered saturated or unsaturated bicyclic 8- to 10-membered heterocyclic ring which contains from 1 to 3 heteroatoms selected from N, O or S wherein N or S can be oxidized or N quaternized; each ring is optionally substituted by one or more substituents selected from C$_{1-4}$ alkyl, C$_{1-4}$ alkoxy, amino, cyano, halogen or hydroxy, N[O$_2$S(CH$_2$)$_n$—W][(CH$_2$)$_k$COOH] where n is 0, 1, 2 or 3 and where k is 1, 2 or 3, NH(CH$_2$)$_k$NH$_2$, where k is 1, 2 or 3, NHC(Ph)$_3$.

N[COOR']$_2$ where R' is C$_{1-4}$ alkyl, preferably CMe$_3$.

In preferred compounds R$^c$ is NH$_2$, NHCOOR (wherein R is C$_{1-4}$ alkyl, preferably CMe$_3$ or benzyl), —NHSO$_2$(CH$_2$)$_{0-2}$—W, (wherein R is phenyl, benzyl or naphthyl), alkyl (preferably Me, Et, benzyl or CPh$_3$), —NH(CH$_2$)$_k$COOH or N[SO$_2$(CH$_2$)$_{0-2}$—W][(CH$_2$)$_{1-2}$COOH] or —NH(CH$_2$)$_{1-3}$NH$_2$.

In the aforementioned compounds salts of amino-derivatives may be employed, for example hydrochloride salts.

The invention also relates to the pharmaceutically acceptable salts of the compounds of formula (I) with anticoagulant activity and to pharmaceutical compositions containing them. The invention also relates to the processes for the preparation of compounds of general formula (I).

Novel compounds are thrombin inhibitors and can be used orally and parenterally. They are useful for inhibiting thrombin and formation of fibrin and also for preventing and inhibiting thrombus formation in man and other mammals. They are used in cardiovascular surgery, for the treatment of disseminated intravascular coagulation in thromboembolism, hemodialysis, unstable angina pectoris, ischemic cerebral disease and as an alternative to heparin in patients with heparin-induced thrombocytopenia.

In acute myocardial infarction novel compounds may be used as an adjunct to thrombolytic therapy.

The pharmaceutical compositions which are the object of the described invention may be formulated as injectable or oral formulations. In addition to the active ingredient they contain different standard additives depending on the use. The pharmaceutical compositions are prepared according to the standard procedures. Dosage, frequency and mode of use depend on a variety of factors, they also depend on individual active ingredient and its pharmacokinetic properties and on patient's condition. These compositions may optionaly include thrombolitic agents, anticoagulants and antiplatelet agents.

The compounds described in the present invention have one or more stereogenic centers wherein an absolute configuration is R or S and can be present in the form of racemates, racemic mixtures, pure entatiomers, mixtures of diastereomers or in the form of pure diastereomers.

The starting heterocyclic compounds for the preparation of the compounds, which are the object of the present invention, are prepared as depicted in Schemes I and II or according to the methods described in the literature.

SCHEME I

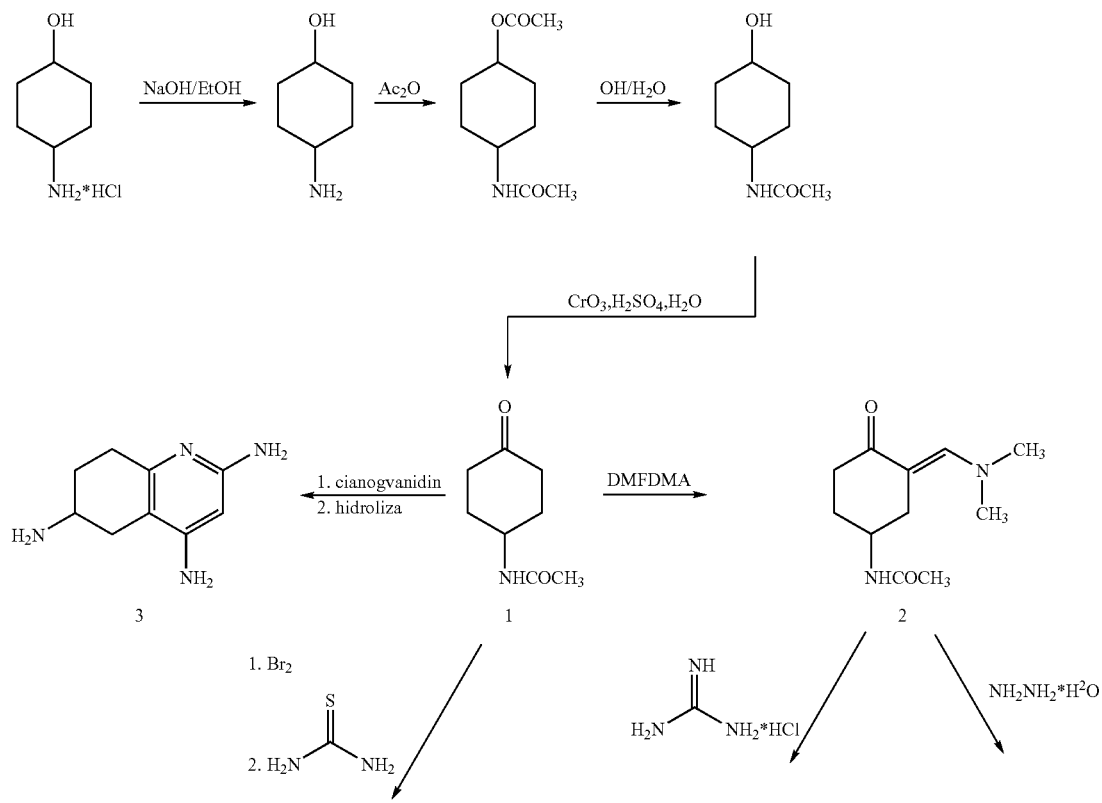

-continued

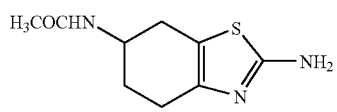 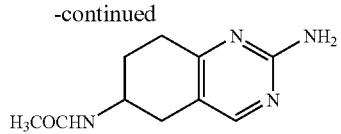 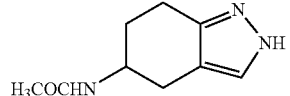

HBr/H₂O ↓    NaOH, H₂O, MeOH ↓    NaOH, H₂O, MeOH ↓

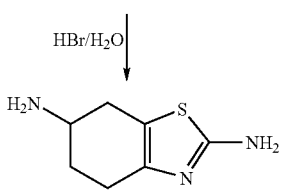 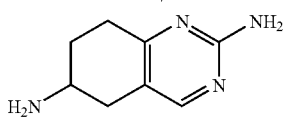 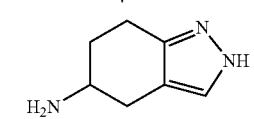

4   5   6

5-Amino-4,5,6,7-tetrahydro-2H-indazole (6) is prepared according to the procedure described in the literature (Bach N. J., Kornfeld E. C., Jones N. D. et al. J. Med. Chem. 1980, 23, 481). 2,6-Diamino-5,6,7,8-tetrahydroquinazoline (5) is prepared by cyclocondensation of suitable enaminoketone (2) (Bach N. J., Kornfeld E. C., Jones N. D. et al. J. Med. Chem. 1980, 23, 481) with guanidine hydrochloride in the presence of sodium ethoxide and subsequent alkaline hydrolysis. 2,4,6Triamino-5,6,7,8-tetrahydroquinazoline (3) is prepared by cyclocondensation of cyanoguanine and N-(4oxocyclohexyl)acetamide (1) according to the procedure described in the articles: Modest E. J., Chatterjee S., Protopapa H. K. J. Am. Chem. Soc. 1965, 87, 1837) in Gangjee A., Zaveri N., Queener S. F. et al. J. Heterocycl. Chem. 1995, 32, 243) and subsequent alkaline hydrolysis. 2,6Diamino4,5,6,7-tetrahydro-1,3-benzothiazole (4) is prepared from N-(4-oxocyclohexyl)acetamide (1) after bromination and cyclization with thiourea, and hydrolysis in hydrobromic acid (Schneider C. S., Mierau J. J. Med. Chem. 1987, 30, 494–498.; Griss G., Schneider C., Hurnaus R. et al. DE 3447075). 2,7-Diamino-4,5,6,7-tetrahydro-1,3-benzothiazole is prepared by reduction of suitable oxime, which is prepared from 2-amino-4,5,6,7-tetrahydro-1,3-benzothiazol-7-one after reaction with hydroxylamine hydrochloride as described, for example, in: Becker D. P., Flynn D. L. Synthesis 1992, 1080–1082. 2-Amino-4,5,6,7-tetrahydro-1,3-benzothiazole-7-one is prepared from 1,3-cyclohexanedione by bromination and subsequent cyclization with thiourea according to the procedure described in the patent (Yoo H. Y., Chung K. J., Chai J. P. et al. WO97/03076). 2,4,5-Triamino-5,6,7,8-tetrahydroquinazoline, 2,5-diamino-5,6,7,8-tetrahydroquinazoline, 4-amino-4,5,6,7-tetrahydro-2H-indazole and 4-amino-4,5,6,7-tetrahydro-2H-isoindole are prepared from 1,3-cyclohexanedione and a suitable reagent for cyclization according to analogous procedures described in the articles: Bach N. J., Kornfeld E. C., Jones N. D. et al. J. Med. Chem. 1980, 23, 481.; Modest E. J., Chattedjee S., Protopapa H. K. J. Am. Chem. Soc. 1965, 87, 1837.; Gangjee A., Zaveri N., Queener S. F. et al. J. Heterocyclic Chem, 1995, 32, 243 and subsequent conversion of the keto group into the amino group, for example, by reductive amination (Abdel-Magid A. F., Carson K. G., Harris B. D. et al. J. Org. Chem. 1996, 61, 3849).

2,4-Diamino-4,5,6,7-tetrahydro-1,3-benzothiazole is prepared from 2-amino-4,5,6,7-tetrahydro-1,3benzothiazol-4-one with ammonia in the presence of a catalyst according to the analogous procedure described in the patent (Schönwald K., Meyer Th., Eishold K. W. DE 2845857). The preparation of 2-amino-4,5,6,7-tetrahydro-1,3-benzothiazol-4-one from 1-amino-cyclohexen-3-one with rhodamine is described in the articles: Schmitz E., Striegler H. J. Prakt. Chem. 1971, 1125–1130 and Schmitz E., Striegler H. J. Prakt. Chem. 1970, 359–365. Alternatively, it may also be proceeded from 2-azidocyclohexanole which by reduction, acetylabon of the amino and hydroxy group, selective hydrolysis of the ester group and oxidation, carried out for example with CrO₃ according to the analogous procedure described in: Curtin D. Y., Schmukler S. J. Am. Chem. Soc. 1955, 77, 1105 is converted to 2-acetamidocyclohexanone, and the latter after bromination, cyclizatian with thiourea and hydrolysis is converted to 2,4-diamino-4,5,6,7-tetrahydro-1,3-benzothiazole. After cyclization of 2-acetamidocyclohexanone with suitable reagents, according to analogous procedures described in articles: Bach N. J., Kornfeld E. C., Jones N. D. et al. J. Med. Chem. 1980, 23, 481.; Modest E. J., Chatteqee S., Protopapa H. K. J. Am. Chem. Soc. 1965, 87, 1837.; Gangjee A., Zaveri N., Queener S. F. et al. J. Heterocycl. Chem, 1995, 32, 243 and subsequent hydrolysis, 2,4,8-triamino-5,6,7,8-tetrahydroquinazoline, 2,8-diamino-5,6,7,8-tetrahydroquinazoline, 7-amino-4,5,6,7-tetrahydro-2H-indazole and 7-amino-4,5,6,7-tetrahydro-2H-isoindole are obtained.

2,6-Diamino-1,3-benzothiazole is prepared by reduction of 2-amino-6-nitro-1,3-benzothiazole according to the procedures described in: Hays S. J., Rice M. J., Ortwine D. F. et al. J. Pharm. Sci. 1994, 83, 1425–1432 and Abdelaal S. M., Kong S.-B., Bauer L. J. Heterocycl. Chem. 1992, 29, 1069–1076.

2,5-Diamino-4,5,6,7-tetrahydro-1H-benzimidazole is prepared from N-(4-oxocyclohexyl)-acetamide and N-acetylguanidine according to, the procedure described for the preparation of 2-aminoimidazoles (Little T. L, Webber S. E. J. Org. Chem. 1994, 59, 7299–7305) and subsequent hydrolysis of the acetamide group. According to the analogous procedure, 2,4-diamino-4,5,6,7-tetrahydro-1H-benzimidazole is prepared from N-(2-oxocyclohexyl)-acetamide.

2,6-Diamino-4,5,6,7-tetrahydro-1,3-benzoxazole is prepared from N-(4-oxocyclohexyl)-acetamide by cyclization with thiourea according to the procedure described for the synthesis of 2-amino-4,5,6,7-tetrahydro-1,3-benzoxazole (Nayer H., Giudicelli R., Menin J. Bull. Soc. Chim. 1967, 2040–2043) and subsequent hydrolysis of the acetamide group. According to the analogous procedure, 2,4-diamino-4,5,6,7-tetrahydro-1,3-benzoxazole is prepared from N-(2-oxocyclohexyl)-acetamide.

Starting from cyclopentane-1,3-dione, cyclopentane-1,3-dione monoethylene acetal and N-(3-oxocyclopentyl)acetamide according to analogous procedures as described above, the amino derivatives of 6,7-dihydro-5H-cyclopenta[d]pyrimidine, 1,4,5,6-tetrahydrocyclopenta[d]-imidazole, 5,6-dihydro-4H-cyclopenta[d][1,3]-thiazole, 5,6-dihydro-4H-cyclopenta[d][1,3]-oxazole, 2,4,5,6-tetrahydrocyclopenta[c]pyrrole and 2,4,5,6-tetrahydrocyclopenta[c]pyrazole are prepared.

As depicted in Scheme II, (1,4-dioxospiro[4.5]decan-8-yl)methanamine is prepared from 1,4-cyohexanedione monoethylene acetal (Becker D. P., Flynn D. L. Synthesis, 1992, 1080) and after acetylation with acetanhydride and removal of ketal protection it is then converted with DMFDMA to enaminoketone (8). 6-(Aminomethyl)-5,6,7,8-tetrahydro-2-quinazolinamine (9) is prepared by cyclocondensation of enaminoketone (8) with guanidine hydrochloride and subsequent alkaline hydrolysis. From the suitable enaminoketone (8), according to analogous procedures as described in the article Bach N. J., Kornfeld E. C., Jones N. D. et al. J. Med. Chem. 1980, 23, 481, 4,5,6,7-tetrahydro-2H-isoindole-5-ylmethanamine (10) and 4,5,6,7-tetrahydro-2H-indazole-5-ylmethanamine (11) are prepared. 6-Aminomethyl)-5,6,7,8-tetrahydro-2,4-quinazolinediamine (13) is prepared by cyclocondensation of cyanoguanidine and N-[(4-oxocyclohexyl)methyl]acetamide (7) according to the analogous procedure in: Modest E. J., Chatterjee S., Protopapa H. K. J. Am. Chem. Soc. 1965, 87, 1837.; Gangjee A., Zaveri N., Queener S. F. et al. J. Heterocycl. Chem. 1995, 32, 243, and subsequent alkaline hydrolysis.

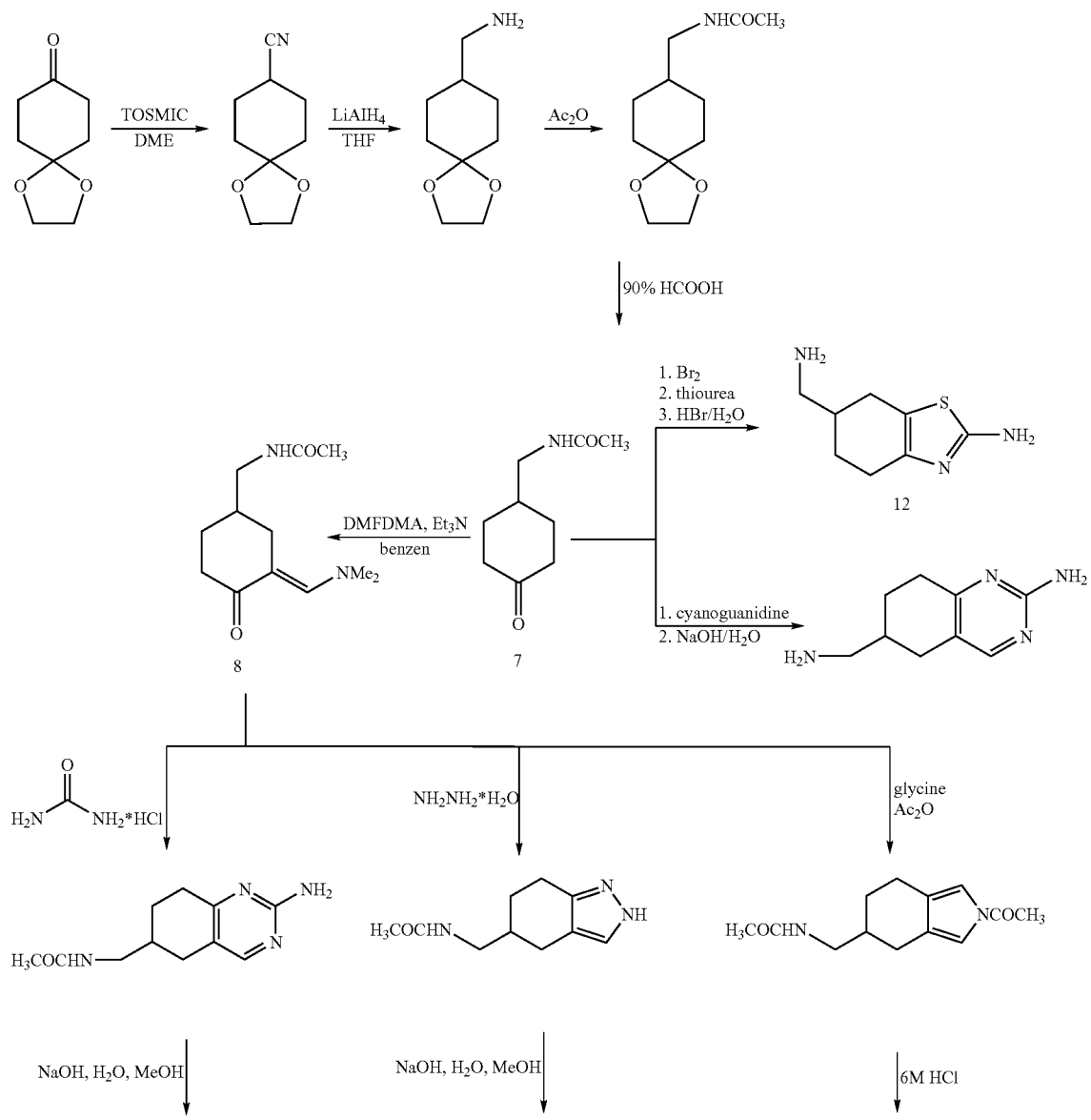

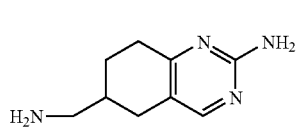 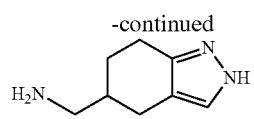 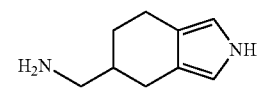

9            10            11

By bromination and cyclization of N-[(4-oxocyclohexyl)methyl]acetamide (7) with thiourea 6-(aminomethyl)-4,5,6,7-tetrahydro-1,3-benzothiazole-2-amine (12) is prepared. 4-(Aminomethyl)-4,5,6,7-tetrahydro-1,3-benzothiazole-2-amine is prepared according to the analogous procedure as described in the article Maillard J., Delaunay P., Langlois M. et al. Eur. J. Med. Chem. 1984, 19, 457–460 from ethyl 2-oxocyclohexanecarboxylatate which is first subjected to bromination and cyclization with thiourea Generated ethyl 2-amino-4,5,6,7-tetrahydro-1,3-benzothiazole-4-carboxylate is reduced to suitable alcohol which is then tosylated at the hydroxyl group and after the reaction with ammonia, 4-(aminomethyl)-4,5,6,7-tetrahydro-1,3-benzothiazole-2-amine is prepared. Employing the above described procedures 4,5,6,7-tetrahydro-2H-isoindole-7-ylmethanamine, 4,5,6,7-tetrahydro-2H-indazole-7-ylmethanamine, 8-(aminomethyl)-5,6,7,8-tetrahydro-2,4-quinazolinediamine and 8-(aminomethyl)-5,6,7,8-tetrahydro-2-quinzolinamine can be prepared from ethyl 2-oxocyclohexanecarboxylate.

Starting from cyclopentane-1,3-dione, cyclopentane-1,3-dione monoethylene acetal and N-(3-oxocyclopentyl)acetamide according to the analogous procedures as described above and depicted in Scheme 2, aminomethyl derivatives of 6,7-dihydro-5H-cyclopenta[d]pyrimidine, 1,4,5,6-tetrahydrocyclopenta[d]-imidazole, 5,6-dihydro-4H-cyclopenta[d][1,3]-thiazole, 5,6-dihydro-4H-cyclopenta[d][1,3]-oxazole, 2,4,5,6-tetrahydrocyklopental[c]pyrrole and 2,4,5,6-tetrahydrocyclopenta[c]pyrazole are prepared.

SCHEME III

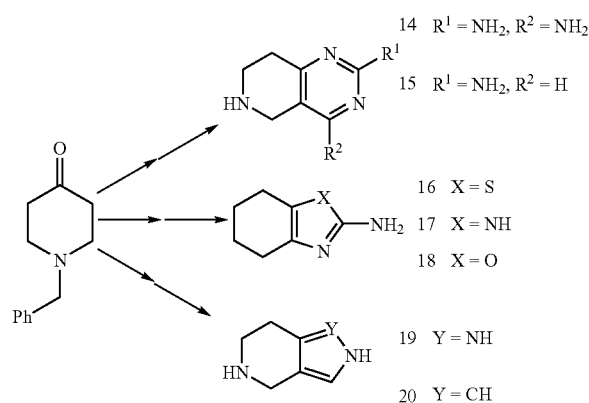

Substituted 5,6,7,8-tetrahydropyrido[4,3-d]pyrimidines (14, $R^1$=NH$_2$, $R^2$=NH$_2$; 15, $R^1$=NH$_2$, $R^2$=H), attached to group A via the position 6, substituted 4,5,6,7-tetrahydro[1,3]thiazolo[5,4-c]pyridine (16, X=S, $R^1$=H or NH$_2$), substituted 4,5,6,7-tetrahydro-3H-imidazo[4,5-c]pyridine (17, X=NH $R^1$=H or NH$_2$), substituted 4,5,6,7-tetrahydro[1,3]oxazolo[5,4-c]pyridine (18, X=O, $R^1$=H or NH$_2$), 4,5,6,7-tetrahydro-2H-pyrazolo[4,3-c]pyridine (19, Y=NH) and 4,5,6,7-tetrahydro-2H-pyrrolo[3,4-c]pyridine (20, Y=CH) (Scheme III) are prepared from 1-benzyl-4-piperidinone according to the procedures of cyclization, depicted in Scheme I, followed by removal of the benzyl group by catalytic hydrogenation.

SCHEME IV

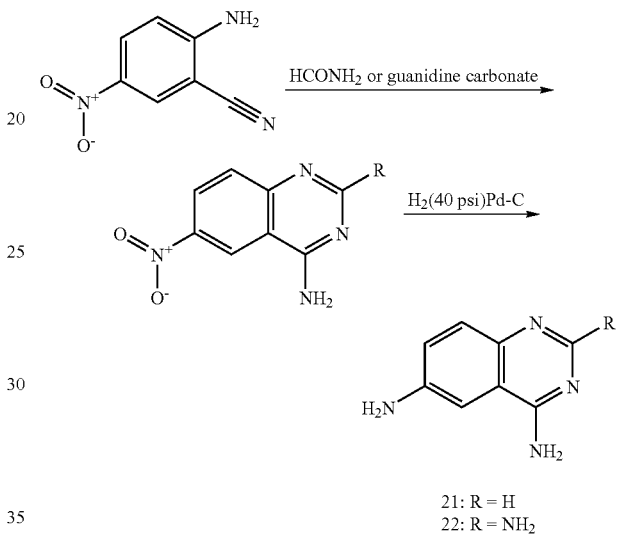

21: R = H
22: R = NH$_2$ 4,6-Quinazolinediamine (21) and 2,4,6-quinazolinetriamine (22) are prepared according to the method described in the literature (Victory P., Borrell J. I., Vidal-Ferran A., Montenegro E., Jimeno M. L. Heterocycles 1993, 36, 2273–2279.; Yan S. J., Weinstock L. T., Cheng C. C. J. Heterocycl. Chem. 1979, 16, 541–544 (Scheme IV). According to the same method 4,7quinazolinediamine and 2,4,7-quinazolinetriamine are prepared from 2-amino -4-nitro-benzonitrile [Houben-Weyl: Hetarenes IV: Vol. E 9b/part 2. 4th ed., Thieme, Stuttgart, New York (1998), p. 1–192]

6-(Aminomethyl)-4-quinazolinamine, 7-(aminomethyl)-4-quinazolinamine, 6-(aminomethyl)-2-quinazolinamine, 7-(aminomethyl)-2-quinazolinamine, 6-(aminomethyl)-2,4-quinazolinediamine and 7-(aminomethyl)-2,4-quinazolinediamine are prepared from 6-(bromomethyl)-4-chloroquinazoline, 7-(bromomethyl)-4-chloroquinazoline, 6-(bromomethyl)-2-chloroquinazoline, 7-(bromomethyl)-2-chloroquinazoline, 6-(bromomethyl)-2,4-dichloroquinazoline or 7-(bromomethyl)-2,4-dichloroquinazoline and ammonia in polar organic solvents at elevated pressure and elevated temperature. The aforementioned 6-bromomethyl- and 7-bromomethylchloroquinazolines are prepared by bromination of 6-methyl-4-chloroquinazoline, 6-methyl-2-chloroquinazoline, 7-methyl-4-chloroquinazoline, 7-methyl-2-chloroquinazoline, 6-methyl-2,4-dichloroquinazoline and 7-methyl-2,4-dichloroquinazoline as, for example, described for the preparation of 6-bromomethyl-4-chloroquinazoline in the patent application EP 566226. The preparation of imidazo[1,2-a]pyridine-6-ylmethanamine is described in the patent application WO9961442.

Compounds of general formula (I), wherein A represents group —CONH— attached to Het with NH fragment or group —CONHCH$_2$— attached to Het with CH$_2$ fragment, are prepared by condensation of fragment B which has a protecting group P or D-CO CO fragment attached to N-atom and the COOH group attached to carbon (in most cases being a stereogenic centre) adjacent to nitrogen to with Het-NH$_2$ or Het-CH$_2$NH$_2$ fragment (Scheme V, Scheme VI). When a protecting group P is attached to N-atom of fragment B, after condensation the protecting group is removed and the obtained compound is condensed with D-COOH fragment (Scheme VI). For condensation, in both examples, conventional reagents may be used for formation of the peptide bond as, for example, dicyclohexylcarbodiimide, 1-(3-dimethylaminopropyl)-3-ethylcarbodiimide (EDC), diphenylphosphorylazide, alkyl chloroformates, etc. (see, for example, Bodanszky M., Bodanszky A. The Practice of Peptide Synthesis, Springer, Berlin, 1994). For the removal of protecting groups conventional procedures can be used as described, for example, in the books: (Green T. W. Protective groups in organic synthesis, John Wiley & Sons, New York, 1980; Kocienski P. J. Protecting groups, Thieme Verlag, Stuttgart, 1994).

SCHEME V

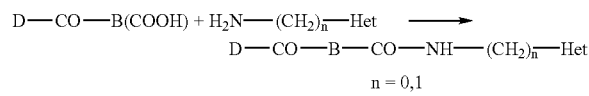

n = 0,1

SCHEME VI

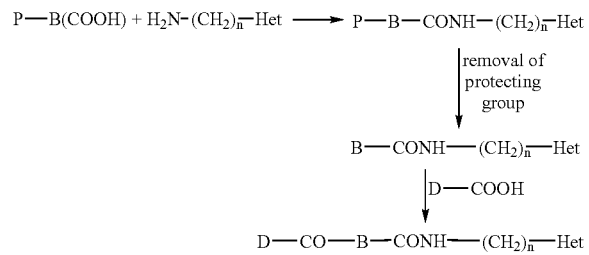

Fragment B-A-Het, wherein A is group —CH$_2$NH— attached to Het with NH fragment or A is group —CH$_2$NHCH$_2$— attached to Het with CH$_2$ fragment, is prepared by reduction amination of aldehydes B—CHO wherein a suitable protecting group is linked to N-atom (the preparation of these compounds is described, for example, in the article Avenell K. Y., Boyfield I., Hadley M. S. et al. Bioorg. Med. Chem. Lett. 1999, 9, 2715), which is introduced and on completed reaction removed according to the method conventionally used in this technical field (Green T. W. Protective groups in organic synthesis, John Wiley & Sons, New York, 1980; Kocienski P. J. Protecting groups, Thieme Verlag, Stuttgart, 1994), with amines Het-NH$_2$ or HetCH$_2$NH$_2$. Reductive amination is a well known reaction described, for example, in the articles: Lane C. F., Synthesis 1975, 135.; Abdel-Magid A. F., Carson K. G., Harris B. D. et al. J. Org. Chem. 1996, 61, 3849).

Fragment B-A-Het, wherein A is group —CH$_2$NHCONH— attached to Het with —NH— fragment, is prepared from aldehyde B—CHO (wherein a suitable protective group P is attached to N, which is introduced and on completed reaction removed according to the methods conventionally used in this technical field), which is subjected to reductive amination with ammonium acetate, as already described, and then by conversion of the obtained amine with ethyl chloroformate, which is carried out according to the analogous procedure as described in the book: Bodanszky M., Bodanszky A. The Practice of Peptide Synthesis, Springer, Berlin, 1994, 92–93. A compound of the type P—B—CH$_2$NHCOOEt is obtained which is attached to Het-NH$_2$ by the conventional procedure. Fragment B-A-Het, wherein A is group —CH$_2$NHCH$_2$CONH— attached to Het with —NH— fragment is prepared according to the analogous procedure but instead of ethyl chloroformate, ethyl bromoacetate is used. In case A is group —CH$_2$NHCOCH$_2$NH— attached to Het with —NH— fragment, first the reaction is carried out between Het-NH$_2$ and ethyl bromoacetate according to the conventional procedures, and then the obtained ester Het-NH—CH$_2$COOEt is converted to a compound B—CH$_2$NHCOCH$_2$NHHet using a compound B—CH$_2$NH$_2$, obtained according to the above described procedure. Fragments B-A-Het, where A represents group —CH$_2$NHCONHCH$_2$—, —CH$_2$NHCH$_2$CONHCH$_2$—, —CH$_2$NHCOCH$_2$NHCH$_2$—, attached to Het by —CH$_2$— fragment, are prepared according to the analogous procedures but instead of Het-NH$_2$, Het-CH$_2$NH$_2$ is used.

Compounds of the type NH(R$^3$)CH(R$^4$)COOR, which serve for introducing fragment B, are prepared by reductive amination of aldehydes or ketones with amino acid esters using sodium cyanoborohydride (Stanton J. L., Gruenfeld N., Babiarz J. E. et al. J. Med. Chem. 1983, 26, 1967) or sodium triacetoxyborohydride (Abdel-Magid A. F., Carson K. G., Harris B. D. et al. J. Org. Chem. 1996, 61, 3849–3862). When R in the above type of compounds represents an alkyl or a benzyl group, the suitable acids can be obtained with alkaline hydrolysis or with catalytic hydrogenation.

Compounds of the type D-COOH, in which R$^a$, R$^b$ and R$^d$ in formula (I) have the defined meaning and R$^c$ represents group —NHO$_2$S(CH$_2$)$_n$—W, are prepared via the reaction of suitable adequately protected amino acids with sulfonyl chlorides W—(CH$_2$)$_n$—SO$_2$Cl according to the method as described, for example, in the article Feng D. M., Gardell S. J., Lewis S. D. et. al. J. Med. Chem. 1997, 40, 3726.

Compounds of the type D-COOH, in which R$^a$, R$^b$ and R$^d$ in formula (I) have the defined meaning and R$^c$ represents group N[O$_2$S(CH$_2$)$_n$—W][(CH$_2$)$_k$COOH], are prepared by alkylating sulfonamides W—(CH$_2$)$_n$—SO$_2$NHCH(R$^d$)COOH, described in the above paragraph, with haloacids X—(CH$_2$)n-COOH or esters thereof (if esters are used, alkaline hydrolysis should be carried after alkylation).

Compounds of type D-COOH, in which R$^a$, R$^b$ and R$^d$ in formula (I) have the defined meaning and R$^c$ represents one of the groups NH(CH$_2$)$_n$CH$_3$,
NH(CH$_2$)$_m$OH,
NH(CH$_2$)$_k$COOH,
NH(CH$_2$)$_n$COOR$^5$,
NH(CH$_2$)$_k$CONR$^6$R$^7$,
NH(CH$_2$)$_k$NH$_2$,
NHC(Ph)$_3$, wherein k, m, n, R$^5$, R$^6$ and R$^7$ have the above defined meaning, are prepared by alkylation of amino acids with conventional alkyl halides, adequately protected ω-hydroxyalkyl halides, adequately protected ω-aminoalkyl halides or alkyl halocarboxylates. The protecting groups can be removed from the obtained products using generally known methods (Green T. W. Protective groups in organic synthesis, John Wiley & Sons, New York, 1980; Kocienski P. J. Protecting groups, Thieme Verlag, Stuttgart, 1994), likewise conventional methods for hydrolysis of esters, formation of peptide linkage or aminolysis of esters, the compounds, in which $R^c$ represents $NH(CH_2)_nCOOR^5$ can be converted to acids $[R^c=NH(CH_2)_kCOOH]$ and amides $[R_c=NH(CH_2)_n CONR^6R^7]$.

Pharmaceutically acceptable salts of the compounds of formula I are prepared by treating the compounds I with acids or bases in suitable organic solvents conventionally used in this technical field.

In Vitro Assays for Determining Proteinase Inhibition

Coagulation Assays

The Anticoagulant effect of thrombin inhibitors was measured by thrombin time (TT), activated partial thromboplastin time (aPTT), and prothrombin time (PT) assays. Inhibitors were added to normal pooled human plasma over a range of concentrations and clotting was recorded in an automated coagulometer (Fibrintimer, Dade/Behring). The concentration of inhibitor that doubled the clotting time was determined for each assay.

1. Thrombin Time (TT)

a) Principle of Method

In a plasma sample thrombin converts fibrinogen into fibrin and the clot is formed. The time for clot formation was measured. Thrombin time is prolonged due to disorders in fibrin polymerisation or due to the presence of thrombin inhibitors.

b) Reagents

Thrombin (Test Thrombin Reagent, 1.5 IU/mL, Dade/Behring): lyophilized bovine thrombin was dissolved in 5 mL of HEPES (25 mmol/L, pH 7.4). The reagent was warmed to 37° C. prior to the assay.

Normal pooled plasma: venous blood from 11 apparently healthy volunteers was collected (1 part 0.11 mol/L sodium citrate solution with 9 parts of blood) and centrifuged immediately at 2000×g for 30 minutes at 4° C. Plasma was removed, pooled and stored in aliquots at −70° C. until use.

Inhibitors: were dissolved in DMSO (10 mM stock solution) and diluted with distilled water to working solutions (the highest concentration 100 µM).

c) Method

Inhibitors (10 µL working solution, concentrations from 2.5 µM to 100 µM) and pooled plasma (90 µL) were incubated at 37° C. for 5 minutes and then thrombin (200 µL) was added. Clot formation was measured in a coagulometer in duplicate.

2. Activated Partial Thromboplastin Time (aPTT)

a) Principle of Method

Incubation of plasma with the optimal quantity of phospholipids and a surface activator leads to activation of factors of the intrinsic coagulation pathway. The addition of calcium ions triggers the coagulation process. The time of fibrin clot formation wass measured. aPTT was used as a screening test for coagulation disorders of the intrinsic coagulation pathway. It is prolonged due to intrinsic coagulation factors deficit or due to the presence of inhibitors.

b) Reagents

Pathromtin SL (Dade/Behring): silicon dioxide particles, vegetable phospholipids, sodium chloride (2.4 g/L), Hepes (14.3 g/L, pH 7.6), sodium azide (<1 g/L). The reagent was used at room temperature (15–25° C.).

Calcium chloride solution: 0.025 mol/L, warmed to 37° C.

Normal pooled plasma: venous blood from 11 apparently healthy volunteers was collected (1 part 0.11 mol/L sodium citrate solution with 9 parts of blood) and centrifuged immediately at 2000×g for 30 minutes at 4° C. Plasma was removed, pooled and stored in aliquots at −70° C. until use.

Inhibitors: were dissolved in DMSO (10 mM stock solution) and diluted with distilled water to working solutions (the highest concentration 100 µM).

c) Method

Inhibitor (10 µL working solution, concentrations from 5 µM to 100 µM) and pooled plasma (90 µL) were incubated at 37° C. for 5 minutes. Pathromtin (100 µL) was added and the sample was incubated for another 2 minutes at 37° C. The addition of calcium chloride (100 µL) triggered the coagulation process and clot formation was detected with a coagulometer in duplicate.

3. Prothrombin Time (PT)

a) Principle of Method

An optimal amount of thromboplastin and calcium are added to plasma sample and the time of fibrin clot formation wass measured. PT is a rapid, sensitive screening test for coagulation disorders of the extrinsic pathway. It is well suited for the induction and monitoring of oral anticoagulant therapy, for diagnosing genetic or acquired deficiencies in coagulation factors and checking the synthesis performance of the liver in hepatic diseases. PT is prolonged due to extrinsic coagulation factors deficit or due to the presence of inhibitors.

b) Reagents

Thromboplastin (Thromborel S, Dade/Behring): was dissolved in 4 mL of distilled water. Reagent was at 37° C. prior to use at least 30 minutes.

Normal pooled plasma: venous blood from 11 apparently healthy volunteers was collected (1 part 0.11 mol/L sodium citrate solution with 9 parts of blood) and centrifuged immediately at 2000×g for 30 minutes at 4° C. Plasma was removed, pooled and stored in aliquots at −70° C. until use.

Inhibitors: were dissolved in DMSO (10 mM stock solution) and diluted with distilled water to working solutions (the highest concentration 100 µM).

c) Method

Inhibitor (10 µL working solution, concentrations from 5 µM to 100 µM) and pooled plasma (90 µL) were incubated at 37° C. for 5 minutes and then Thromborel S (200 µL) was added. Clot formation was measured with a coagulometer in duplicate.

Enzyme Assay

The enzyme inhibitory effect of the compounds can be identified by determination of inhibition constant Ki. It denotes the degree of dissociation of the enzyme-inhibitor complex. Low dissociation constant means high potency of inhibitor. Ki can be determined during reaction of the enzyme with a specific chromogenic substrate which under hydrolysis by the enzyme develops color. Reaction in time is recorded by spectrophotometry and Ki is calculated from kinetic parameters (Vmax, Km, reaction rate).

1. Determination of Thrombin Ki a) Principle of Method

The ability of a compound to act as an inhibitor of human thrombin catalytic activity was assessed by determination of Ki.

b) Reagents

Buffer: HBSA, pH 7.5 (10 mM Hepes, 150 mM NaCl, 0.1% w/v bovine serum albumin)

Substrate (S-2238: H-D-Phe-Pip-Arg-pNA HCl, 25 mg; Chromogenix): dissolved in distilled water to 1 mM concentration. (Km is 2.6 µM)

Human thrombin (308 NIH; Sigma): dissolved in saline to give a stock solution of 20 NIH/mL.

Inhibitors: were dissolved in DMSO (10 mM stock solution) and diluted with distilled water to working solutions (the highest final concentration of DMSO was 3%).

c) Method

A mixture of 50 µL of buffer, 50 µL of inhibitor in water (final concentrations from 10 to 100 µM) and 50 µL of thrombin (0.5 NIH U/mL f.c.) was incubated for 15 minutes at room temperature. The reaction was started with 50 µL of S-2238 (20 µM or 40 µM f.c.) and the absorbance of each sample at 405 nm (at 25° C.) was measured in triplicate every 10 seconds for a period of 15 minutes using a microtiter plate reader (Tecan Sunrise).

Thrombin activity was determined from the change in absorbance in the linear part of the velocity graph. Ki was calculated according to Cheng and Prussof (Biochem Pharmacol, 1973) where Ki is $IC_{50}/(1+S/Km)$. The Km for the substrate was determined under the test conditions with at least 6 substrate concentrations varying around Km and calculated with the non-linear regression programme Curve expert.

2. Determination of Trypsin Ki a) Principle

The ability of a compound to act as an inhibitor of trypsin catalytic activity was assessed by determination of Ki.

b) Reagents

Buffer: HBSA, pH 7.5 (10 mM Hepes, 150 mM NaCl, 0.1% w/v bovine serum albumin)

Substrate (S-2222: N-benzoyl-Ile-Glu-Gly-Arg-pNA HCl, 25 mg; Chromogenix): dissolved in distilled water to 2 mM concentration. (Km is 21 µM)

Trypsin (6000 E/mg prot.; Sigma): dissolved in distilled water to give a stock solution of 300 E/mL.

Inhibitors: were dissolved in DMSO (10 mM stock solution) and diluted with distilled water to working solution (the highest final concentration of DMSO was 10%).

c) Method

50 µL of buffer, 50 µL of test compound in water (final concentrations from 50 to 300 µM) and 50 µL of trypsin (3 mE/mL f.c.) were incubated for 15 minutes at room temperature. The reaction was started with 50 µL of S-2222 (50 µM or 100 µM f.c.) and the absorbance of each sample at 405 nm (at 25° C.) was measured in triplicates every 10 seconds for a period of 15 minutes using a microtiter plate reader (Tecan Sunrise).

Trypsin activity was determined from the change in absorbance in the linear part of velocity graph. Ki was calculated according to Cheng and Prussof (Biochem Pharmacol, 1973) where Ki is, $IC_{50}/(1+S/Km)$. The Km for the substrate was determined under test conditions with at least 6 substrate concentrations varying around Km and calculated with the non-linear regression program Curve expert.

3. Selectivity to Thrombin

By the use of other serine protease like trypsin with the appropriate chromogenic substrate, selectivity of inhibitors with respect to thrombin was determined. Selectivity of an inhibitor is expressed as a ratio of Ki for trypsin to Ki for thrombin.

The invention is further described by means of the following examples, but not in any limitative case.

EXAMPLE 1

Methyl (2S)-2-({(2R)-2-[(benzylsulfonyl)amino]-3-phenylpropanoyl}amino)propanoate

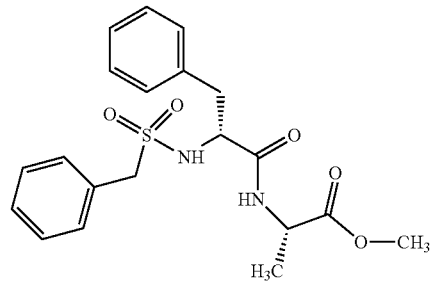

To a solution of N-(benzylsulfonyl)-D-Phe-OH (1.56 g, 5.0 mmol) and L-Ala methyl ester hydrochloride (0.628 g, 4.5 mmol) in 11 mL of DMF, was added HOBt (0.770 g, 5.0 mmol). The pH of the solution was adjusted with N-methylmorpholine to 8, followed by the addition of EDC (0.978 g, 5.0 mmol). The reaction mixture was stirred at room temperature overnight. The solvent was evaporated, EtOAc and a saturated solution of $NaHCO_3$ were added to the residue. The organic layer was washed with brine, dried over $MgSO_4$, filtered, and the solvent was removed under reduced pressure to give 1.73 g of yellow solid (95%).

IR (KBr): ν=3281, 2952, 1736, 1648, 1543, 1456, 1317, 1221, 1151, 1125, 952, 790, 749, 698, 548 $cm^{-1}$. MS (EI): m/z (%) 405 ($MH^+$, 47), 91 (100). $^1$H-NMR (300 MHz, DMSO-$d_6$): δ 1.19 (d, 3H, J=7.16 Hz, $AlaCH_3$), 2.80 (2.92) ($ABX_{system}$, 2H, $J_{AB}$=13.56, $J_{AX}$=9.04, $J_{BX}$=6.03, $PheCH_2$), 3.58 (s, 3H, $COOCH_3$), 4.01 ($AB_{system}$, 2H, $J_{AB}$=13.56 Hz, $CH_2Ph$), 4.15–4.36 (m, 2H, AlaCH, PheCH), 7.19–7.35 (m, 10H, 2 Ph), 7.67 (d, 1H, J=9.04 Hz, NH), 8.61 (d, 1H, J=7.16 Hz, NH).

EXAMPLE 2

(2S)-2-({(2R)-2-[(benzylsulfonyl)amino]-3-phenylpropanoyl}amino)propanoic acid

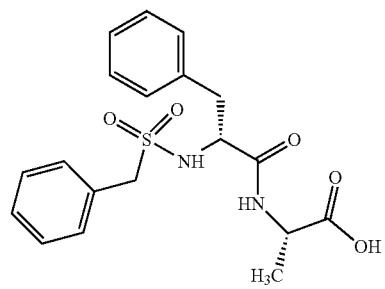

N-(Benzylsulfonyl)-D-Phe-L-Ala-OMe (1.70 g, 4.21 mmol) was dissolved in 100 mL of MeOH/$H_2O$ (1/1) and 2.5 mL 2.2 M solution of LiOH was added dropwise to adjust the pH to 12–13. After stirring overnight, pH of the reaction mixture was adjusted to 7, using diluted solution of $KHSO_4$. Methanol was evaporated, the residual water phase was acidified with $KHSO_4$ to pH=2, extracted with ethylacetate, washed with brine, dried over $Na_2SO_4$, filtered, and evaporated under reduced pressure. The procedure gave 0.950 g of faint yellow solid (58%).

IR (KBr): ν=3321, 2930, 1734, 1654,1541, 1497, 1456, 1321, 1152, 1031, 950, 783, 747, 699, 621, 543 cm$^{-1}$. MS (EI): m/z (%) 391 (M$^+$, 100). $^1$H-NMR (300 MHz, DMSO-d$_6$): δ 1.15–1.21 (m, 3H, AlaCH$_3$), 2.80 (2.91) (ABX$_{system}$, 2H, J$_{AX}$=9.04, J$_{BX}$=6.03, J$_{AB}$=13.56, PheCH$_2$), 4.03 (AB$_{system}$, 2H, J$_{AB}$=13.56 Hz, CH$_2$Ph), 4.17–4.35 (m, 2H, AlaCH, PheCH), 7.20–7.33 (m,10H, 2 Ph), 7.65 (d, J=9.04 Hz, 1H, NH), 8.50 (d, J=7.53 Hz, 1H, NH), 12.62 (s, 1H, COOH).

EXAMPLE 3

Methyl (2S)-1-[2-(tritylamino)acetyl]-2-pyrrolidinecarboxylate

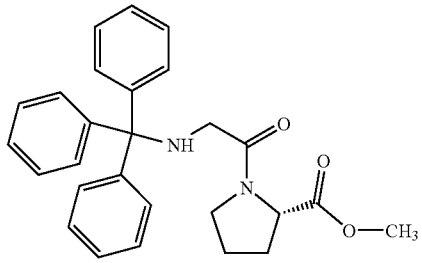

To a solution of N-(trityl)-Gly (3.11 g, 10 mmol) and L-Pro-OMe (1.16 g, 9.0 mmol) in 22.5 mL of DMF was added HOBt (1.55 g, 10 mmol). N-methylmorpholine was used to adjust pH of the solution to 8, followed by the addition of EDC (1.96 g, 10.0 mmol). Reaction mixture was stirred at room temperature overnight. The solvent was evaporated, ethylacetate and saturated solution of NaHCO$_3$ were added to the residue. Organic layer was washed with brine, dried over MgSO$_4$, filtered and the solvent was removed under reduced pressure. The procedure gave 3.81 g of white solid (91%).

MS (EI): m/z (%) 428 (M$^+$, 65), 243 (100). $^1$H-NMR (300 MHz, DMSO-d$_6$): δ 1.70–2.15 (2*m, 4H, ProCH$_2$β, ProCH$_2$γ), 2.90–3.40 (2*m, 4H, GlyCH$_2$, ProCH$_2$δ), 3.59 (s, 3H, CH$_3$) 4.1–4.17 (m, 1H, ProCHα), 7.19–7.42 (m, 16H, 3×(trityl)Ph, GlyNH).
* cis/trans conformers

EXAMPLE 4

(2S)-1-[2-(Tritylamino)acetyl]-2-pyrrolidinecarboxylic acid

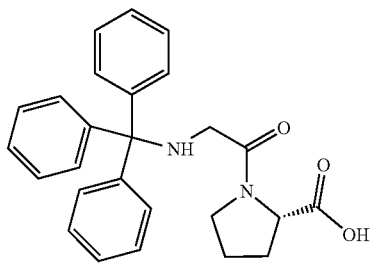

N-(Trityl)-Gly-L-Pro-OMe (3.0 g, 7.0 mmol) was dissolved in 200 mL of MeOH, 10 mL of water and 4.1 mL of 2.2 M LiOH were added dropwise to adjust pH to 12–13. After stirring overnight, the pH of the reaction mixture was adjusted to 7 with diluted solution of KHSO$_4$. Methanol was evaporated under reduced pressure, water phase was acidified with KHSO$_4$ to pH=5, extracted with ethhyl acetate, washed with brine, dried over Na$_2$SO$_4$, filtered and evaporated under reduced pressure to gave 2.41 g crystalline white solid (83%).

Melting point: 80–83° C. IR (KBr): ν=3416, 3057, 1734, 1645, 1447, 1194, 1034, 751, 703 cm$^{-1}$. MS: m/z (%) 413 (MH$^+$, 58), 243 (100). $^1$H-NMR (300 MHz, DMSO-d$_6$): δ 1.90–2.15 (2*m, 4H, ProCH$_2$β, ProCH$_2$γ), 2.8–3.4 (2*m, 4H, GlyCH$_2$, ProCH$_2$δ), 4.1–4.17 (m, 1H, ProCHα), 7.19–7.42 (m, 16H, 3×(trityl)Ph, GlyNH).

EXAMPLE 5

(±)-5,6,7,8-Tetrahydro-2,6-quinazolinediamine

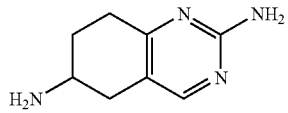

1. Preparation of (±)-N-(2-amino-5,6,7,8tetrahydro-6-quinazolinyl)acetamide

To a solution of sodium ethoxide (0.437 g, 19 mmoles) in 50 mL of absolute ethanol, guanidine hydrochloride (1.82 g, 19 mmoles) was added. After stirring for 30 minutes, a solution of N-[3-[(dimethylamino)methylidene]-4-oxocyclohexyl]acetamide (4.0 g, 19 mmoles) in absolute ethanol was added and the reaction mixture was refluxed under argon atmosphere for 3 hours. The separated solid was collected by filtration to give 3.38 g (87%) of white solid compound.

Melting point: 256–258° C. IR (KBr): ν=3398, 3319, 3212, 3050, 2944, 1647, 1625, 1596, 1558, 1477, 1456, 1375, 1287, 1192, 1099, 1047, 868, 793 cm$^{-1}$. MS (FAB): m/z (%) 207 (MH$^+$, 40), 147 (100). $^1$H-NMR (300 MHz, DMSO-d$_6$): δ 1.60–1.73 (m, 1H, CH$_2$), 1.80 (s, 3H, NHCOCH$_3$), 1.83–1.94 (m, 1H, CH$_2$), 2.33–2.41 (m, 1H, CH$_2$), 2.60–2.77 (m, 3H, CH$_2$, CH$_2$), 3.82–3.96 (m, 1H, 6-CH), 6.24 (s, 2H, 2-NH$_2$), 7.88 (d, 1H, J=6.78 Hz, NHCO), 7.93 (s, 1H, 4-CH). Analysis for C$_{10}$H$_{14}$N$_4$O: Calcd: 58.24%; C, 6.84%; H, 27.18%; N. Found: 57.88%; C, 6.77%; H, 26.91%; N.

2. Preparation of (±)-5,6,7,8-tetrahydro-2,6-quinazolinediamine

A solution of N-(2-amino-5,6,7,8-tetrahydro-6-quinazolinyl)-acetamide (3.0 g, 14.6 mmoles) and sodium hydroxide (30 g, 0.75 moles) in a mixture of water (30 mL) and methanol (90 mL) was refluxed for 16 hours. Water was added, and the mixture was extracted with dichloromethane. The organic extract was washed with brine, dried over sodium sulfate, and the solvent was evaporated under reduced pressure to give 1.40 g (58%) of white solid.

Melting point: 178–181° C. IR (KBr): ν=3412, 1652, 1602, 1558, 1487, 1428, 1362, 1258, 1209, 1103, 1060, 1013, 952, 805, 786, 752, 719 cm$^{-1}$. MS (EI): m/z (%) 164 (M$^+$, 100). $^1$H-NMR (300 MHz, DMSO-d$_6$): δ 1.41–1.55 (m, 1H, CH$_2$), 1.80–1.92 (m, 1H, CH$_2$), 2.16–2.24 (m, 1H, CH$_2$), 2.53–2.69 (m, 3H, CH$_2$, CH$_2$), 2.91–3.02 (m, 1H, 6-CH), 6.18 (s, 2H, 2-NH$_2$), 7.90 (s, 1H, 4-CH). Analysis for C$_8$H$_{12}$N$_4$: Calcd: 58.51%; C, 7:37%; H, 34.12%; N. Found: 58.09%; C, 7.11%; H, 33.91%; N.

EXAMPLE 6

(2S)-N-(2-Amino-5,6,7,8-tetrahydro-6-quinazolinyl)-1-{(2R)-2-[(benzylsulfonyl)amino]-3-phenylpropanoyl}-2-pyrrolidinecarboxamide

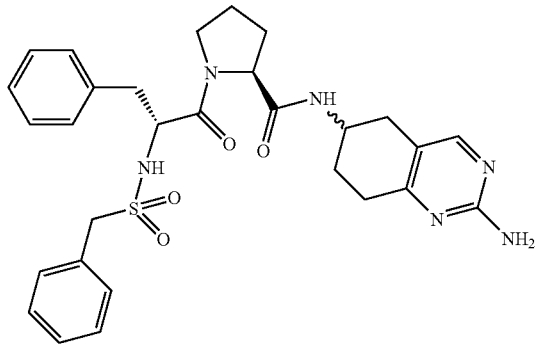

To a solution of N-(benzylsulfonyl)-D-Phe-L-Pro-OH (219 mg, 0.53 mmol) and 2,6-diamino-5,6,7,8-tetrahydroquinazoline (82 mg, 0.50 mmol) in 1.1 mL of DMF was added HOBt (80 mg, 0.53 mmol). The pH of the solution was adjusted with N-methylmorpholine to 8 (moist pH paper) then EDC (101 mg, 0.53 mmol) was added and the reaction mixture was stirred at room temperature overnight. Ethyl acetate (30 mL) was added and the organic phase was washed with NaHCO$_3$ (3×10 mL), brine (3×10 mL) and dried over MgSO$_4$. The solvent was evaporated under reduced pressure and the product was further purified by column chromatography on Florisil using CHCl$_3$/3–5% MeOH as eluent to yield 245 mg (87%) of the title compound and was obtained as a white solid.

Melting point: 117–120° C. IR (KBr): ν=3442, 1636, 1557, 1456, 1318, 1200, 1152, 1125, 945, 784, 699, 545 cm$^{-1}$. MS (FAB): m/z (%) 563 (MH$^+$, 53).

EXAMPLE 7 tert-Butyl (1R)-2-((2S)-2-{[(2-(amino-5,6,7,8-tetrahydro-6-quinazolinyl)amino]carbonyl}pyrrolidinyl)-1-benzyl-2-oxoethylcarbamate

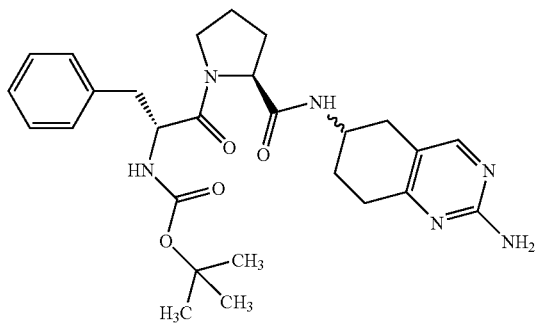

The title compound was prepared from Boc-D-Phe-L-Pm-OH and 2,6-diamino-5,6,7,8-tetrahydroquinazoline according to the procedure described in EXAMPLE 6. The product was obtained as a white solid.

Yield: 77% Melting point: 110–113° C. IR (KBr): ν=3477, 1648, 1541, 1457, 1367, 1252, 1166, 750, 701 cm$^{-1}$. MS (FAB): m/z (%) 509 (MH$^+$, 31).

EXAMPLE 8

(2S)-1-[(2R)-2-Amino-3-phenylpropanoyl]-N-(2-amino-5,6,7,8-tetrahydro-6-quinazolinyl)-2-pyrrolidinecarboxamide dihydrochloride

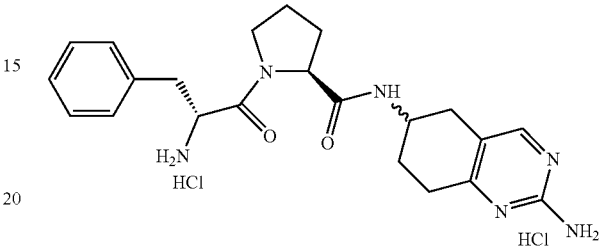

HCl gas was bubbled for 50 minutes through a solution of tert-butyl (1R)-2-((2S)-2-{[(2-amino-5,6,7,8-tetrahydro-6-quinazolinyl)amino]carbonyl}pyrrolidinyl)-1-benzyl-2-oxoethylcarbamate (240 mg, 0.47 mmol) in 15 mL of anhydrous acetic acid at room temperature. Acetic acid was evaporated under reduced pressure and the residue was triturated several times with diethyl ether to yield 141 mg (62%) of the title compound as a white solid.

Melting point: 205–208° C. IR (KBr): ν=3421, 1654, 1541, 1456, 1362, 1202, 948, 764, 704 cm$^{-1}$. MS (FAB): m/z (%) 409 (MH$^+$, 37).

EXAMPLE 9

(2S)-1-{(2R)-2-[(Benzylsulfonyl)amino]-3-phenylpropanoyl}-N-(4,5,6,7-tetrahydro-2H-indazol-5-yl)-2-pyrrolidinecarboxamide

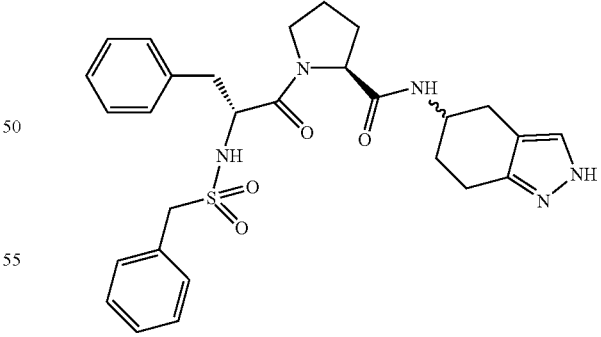

The title compound was obtained as a white solid from N-(benzylsulfonyl)-D-Phe-L-Pro-OH and 5-amino-4,5,6,7-tetrahydro-2H-indazole dihydrochloride using the procedure of EXAMPLE 6.

Yield: 78% Melting point: 114–116° C. IR (KBr): ν=3482, 1651, 1541, 1456, 1318, 1154, 955, 700, 544 cm$^{-1}$. MS (FAB): m/z (%) 536 (MH$^+$, 49).

EXAMPLE 10 tert-Butyl (1R)-1-benzyl-2-oxo-2-{(2S)-2-[(4,5,6,7-tetrahydro-2H-indazol-5-ylamino)carbonyl]pyrrolidinyl}ethylcarbamate

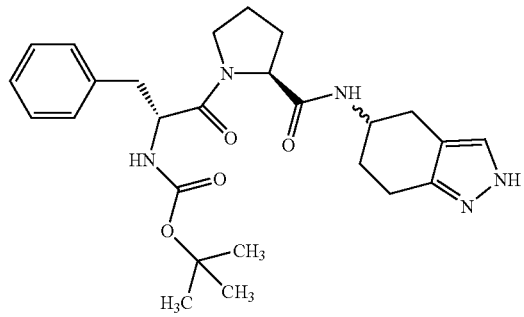

The title compound was prepared from Boc-D-PheL-Pro-OH and 5-amino-4,5,6,7-tetrahydro-2H-indazole dihydrochloride using the procedure of EXAMPLE 6, and was obtained as a white solid.

Yield: 80% Melting point: 108–110° C. IR (KBr): ν=3464, 1636, 1540, 1456, 1367, 1252, 1165, 1089, 957, 749, 702 cm$^{-1}$. MS (FAB): m/z (%) 482 (MH$^+$, 66).

EXAMPLE 11

(2S)-1-[(2R)-2-Amino-3-phenylpropanoyl]-N-(4,5,6,7-tetrahydro-2H-indazol-5-yl)-2-pyrrolidinecarboxamide dihydrochloride

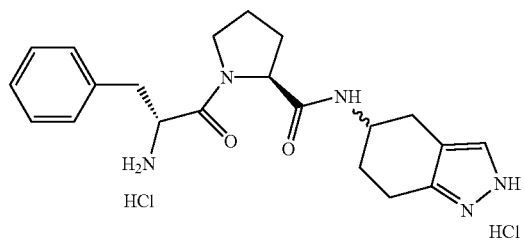

The title compound was prepared from tert-butyl (1R)-1-benzyl-2-oxo-2-{(2S)-2-[(4,5,6,7-tetrahydro-2H-indazol-5-ylamino)carbonyl]pyrrolidinyl}ethylcarbamate using the procedure of EXAMPLE 8, and was obtained as a white solid.

Yield: 77% Melting point: 203–206° C. IR (KBr): ν=3417, 1639, 1453, 1362, 1199, 1083, 919, 761, 703 cm$^{-1}$. MS (FAB): m/z (%) 382(MH$^+$, 100).

EXAMPLE 12

(2S)-N-[(2-Amino-5,6,7,8-tetrahydro-6-quinazolinyl)methyl]-1-{(2R)-2-[(benzylsulfonyl)amino]-3-phenylpropanoyl}-2-pyrrolidinecarboxamide

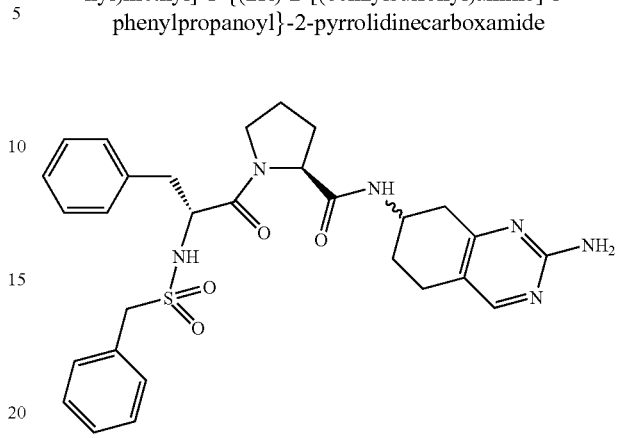

The title compound was prepared from N-(benzylsulfonyl)-D-Phe-L-Pro-OH and 6-(aminomethyl)-5,6,7,8-tetrahydro-2-quinazolinamine using the procedure of EXAMPLE 6, and was obtained as a white solid.

Yield: 87% Melting point: 118–121° C. IR (KBr): ν=3464, 1636, 1558, 1541, 1457, 1318, 1125, 952, 699 cm$^{-1}$. MS (FAB): m/z (%) 577(MH$^+$, 47).

EXAMPLE 13 tert-Butyl (1S)-2-((2S)-2-{[(2-amino-5,6,7,8-tetrahydro-6-quinazolinyl)amino]carbonyl}pyrrolidinyl)-1-benzhydryl-2-oxoethylcarbamate

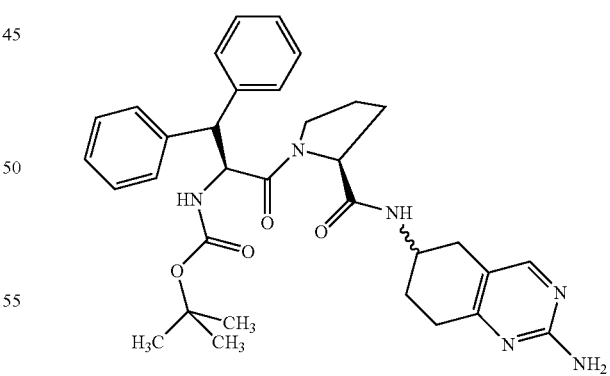

The title compound was prepared from Boc-L-3,3-(Ph)$_2$-Ala-L-Pro-OH and 2,6-diamino-5,6,7,8-tetrahydroquinazoline using the procedure of EXAMPLE 6, and was obtained as a white solid.

Yield: 98% Melting point: 127–130° C. IR (KBr): ν3418, 1649, 1541, 1457, 1367, 1250, 1166, 864, 752, 701 cm$^{-1}$. MS (FAB): m/z (%) 585 (MH$^+$, 52).

EXAMPLE 14 tert-Butyl (1R)-2-((2S)-2-{[(2-amino-5,6,7,8-tetrahydro-6-quinazolinyl)amino]carbonyl}pyrrolidinyl)-1-(3,4-dichlorobenzyl)-2-oxoethylcarbamate

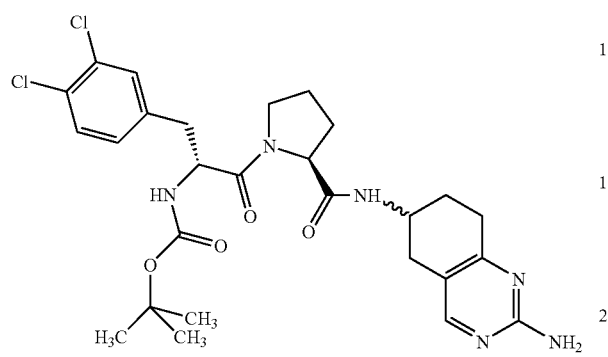

The title compound was prepared from Boc-D-3,4-Cl$_2$-Phe-L-Pro-OH and 2,6-diamino-5,6,7,8-tetrahydroquinazoline using the procedure of EXAMPLE 6, and was obtained as a white solid.

Yield: 94% Melting point: 114–117° C. IR (KBr): ν3447, 2977, 1648, 1557, 1472, 1251, 1165, 1029, 667 cm$^{-1}$. MS (FAB): m/z (%) 577 (MH$^+$, 95).

EXAMPLE 15 tert-Butyl (1S)-1-benzhydryl-2-oxo-2-{(2S)-2-[(4,5,6,7-tetrahydro-2H-indazol-5-ylamino)carbonyl]pyrrolidinyl}ethylcarbamate

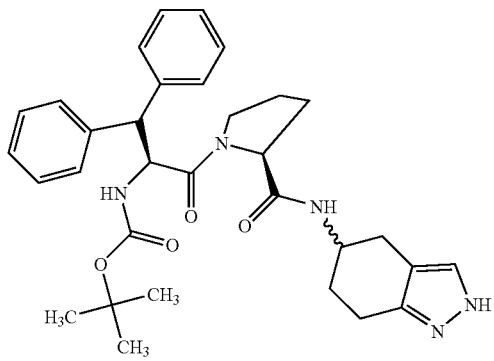

The title compound was prepared from Boc-L-3,3-(Ph)$_2$-Ala-L-Pro-OH and 5-(amino-4,5,6,7-tetrahydro-2H-indazole-dihydrochloride using the procedure of EXAMPLE 6, and was obtained as a white solid.

Yield: 73% Melting point: 127–130° C. IR (KBr): ν3448, 1649, 1540, 1454, 1367, 1250, 1166, 1092, 957, 861, 751, 701 cm$^{-1}$. MS (FAB): m/z (%) 558 (MH$^+$, 60).

EXAMPLE 16 tert-Butyl (1R)-1-(3,4dichlorobenzyl)-2-oxo-2-{(2S)-2-[(4,5,6,7-tetrahydro-2H-indazol-5-ylamino)carbonyl]pyrrolidinyl}ethylcarbamate

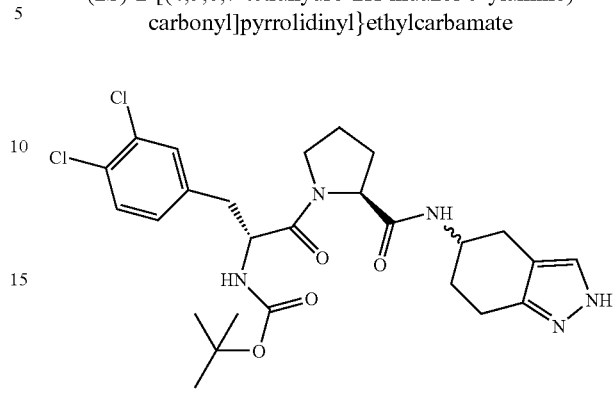

The title compound was prepared from Boc-D-3,4-Cl$_2$-Phe-L-Pro-OH and 5-amino-4,5,6,7-tetrahydro-2H-indazole dihydrochloride using the procedure of EXAMPLE 6, and was obtained as a white solid.

Yield: 54% Melting point: 116–119° C. IR (KBr): ν3419, 2976, 1648, 1540, 1455, 1367, 1251, 1165, 1029, 957, 753, 599 cm$^{-1}$. MS (FAB): m/z (%) 550 (MH$^+$, 40).

EXAMPLE 17

(2S)-1-[(2S)-2-Amino-3,3-diphenylpropanoyl]-N-(2-amino-5,6,7,8-tetrahydro-6-quinazolinyl)-2-pyrrolidinecarboxamide dihydrochloride

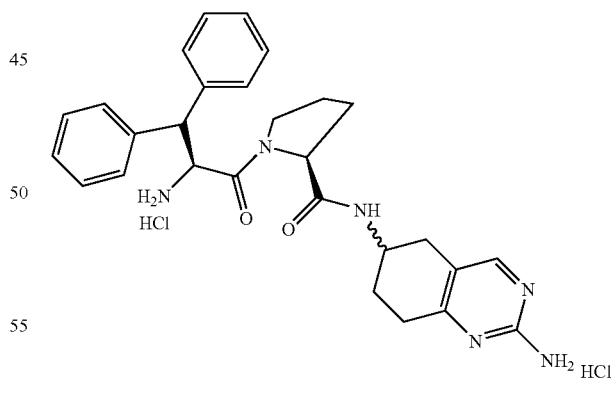

The title compound was prepared from tert-butyl (1S)-2-((2S)-2-{[(2-amino-5,6,7,8-tetrahydro-6-quinazolinyl)amino]carbonyl}pyrrolidinyl)-1-benzhydryl-2-oxoethylcarbamate using the procedure of EXAMPLE 8, and was obtained as a white solid.

Yield: 98% Melting point: 212–215° C. IR (KBr): ν3415, 1645, 1558, 1456, 1397, 1161, 617 cm$^{-1}$. MS (FAB): m/z (%) 485 (MH$^+$, 64).

EXAMPLE 18

(2S)-1-[(2R)-2-Amino-3-(3,4dichlorophenyl)propanoyl]-N-(2-amino-5,6,7,8-tetrahydro-6-quinazolinyl)-2-pyrrolidinecarboxamide dihydrochloride

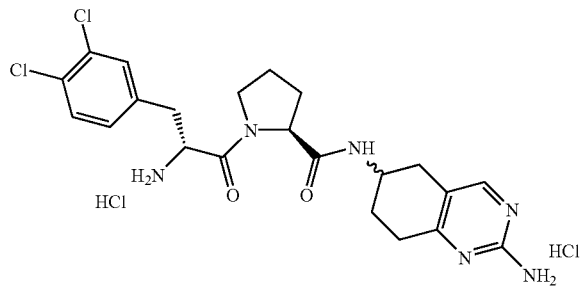

The title compound is prepared from tert-butyl (1R)-2-((2S)-2-{[(2-amino-5,6,7,8-tetrahydro-6-quinazolinyl)amino]carbonyl}pyrrolidinyl)-1-(3,4-dichlorobenzyl)-2-oxoethylcarbamate using the procedure of EXAMPLE 8, and was obtained as a white solid.

Yield: 93% Melting point: 201–204° C. IR (KBr): ν3417, 1650, 1541, 1472, 1396, 1241, 1032, 828, 593 cm$^{-1}$. MS (FAB): m/z (%) 477 (MH$^+$, 50).

EXAMPLE 19

(2S)-1-[(2S)-2-Amino-3,3-diphenylpropanoyl]-N-(4,5,6,7-tetrahydro-2H-indazol-5-yl)-2-pyrrolidinecarboxamide dihydrochloride

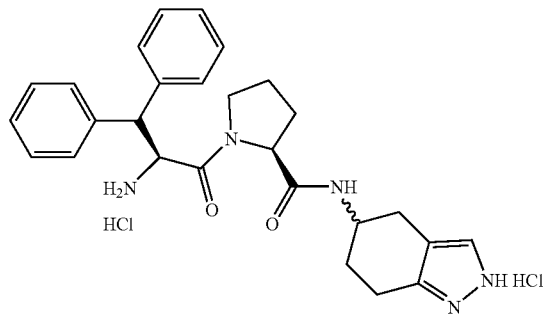

The title compound was prepared from tert-butyl (1S)-1-benzhydryl-2-oxo-2-{(2S)-2-[(4,5,6,7-tetrahydro-2H-indazol-5-ylamino)carbonyl]pyrrolidinyl}ethylcarbamate using the procedure of EXAMPLE 8, and was obtained as a white solid.

Yield: 95% Melting point: 195–198° C. IR (KBr): ν3415, 2930, 1649, 1541, 1453, 1341, 1237, 1084, 753, 704 cm$^{-1}$. MS (FAB): m/z (%) 458 (MH$^+$, 87).

EXAMPLE 20

(2S)-1-[(2R)-2-Amino-3-(3,4-dichlorophenyl)propanoyl]-N-(4,5,6,7-tetrahydro-2H-indazol-5-yl)-2-pyrrolidinecarboxamide dihydrochloride

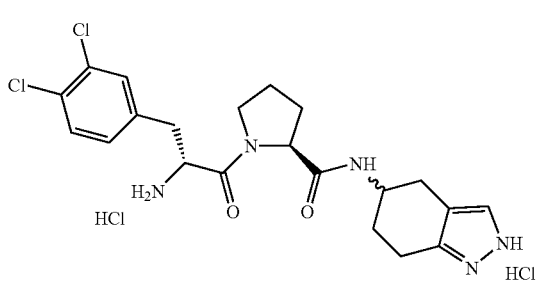

The title compound was prepared from tert-butyl (1R)-1-(3,4dichlorobenzyl)-2-oxo-2-{(2S)-2-[(4,5,6,7-tetrahydro-2H-indazol-5-ylamino)carbonyl]pyrrolidinyl}ethylcarbamate using the procedure of EXAMPLE 8, and was obtained as a white solid.

Yield: 80% Melting point: 199–202° C. IR (KBr): ν3417, 1645, 1541, 1472, 1263, 1134, 1032, 598 cm$^{-1}$. MS (FAB): m/z (%) 450 (MH$^+$, 39).

EXAMPLE 21

(2S)-N-(2-Amino-5,6,7,8-tetrahydro-6-quinazolinyl)-1-{(2R)-2-[(benzylsulfonyl)amino]-3-cyclohexylpropanoyl}-2-pyrrolidinecarboxamide

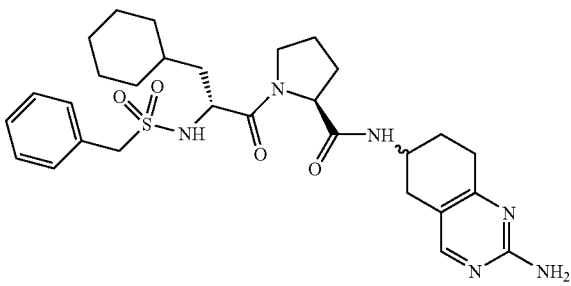

The title compound was prepared from N-(benzylsulfonyl)-D-(cyclohexyl-Ala)-L-Pro-OH and 5,6,7,8-tetrahydro-2,6-quinazolinediamine using the procedure of EXAMPLE 6, and was obtained as a white solid.

Yieldk: 53% Melting point: 114–117° C. IR (KBr): ν3415, 2925, 1641, 1541, 1457, 1149, 615 cm$^{-1}$. MS (FAB): m/z (%) 569 (MH$^+$, 55).

EXAMPLE 22

(2S)-1-{(2R)-2-[(Benzylsulfonyl)amino]-3-cyclohexylpropanoyl}-N-(4,5,6,7-tetrahydro-2H-indazol-5-yl)-2-pyrrolidinecarboxamide

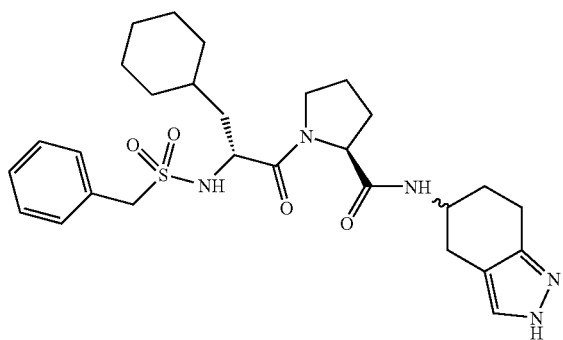

The title compound was prepared from N-(benzylsulfonyl)-D-(cyclohexyl-Ala)-L-Pro-OH and 5-amino-4,5,6,7-tetrahydro-2H-indazole dihydrochloride using the procedure of EXAMPLE 6, and was obtained as a white solid.

Yield: 81% Melting point: 106–109° C. IR (KBr): v3429, 2925, 2851, 1642, 1544, 1448, 1319, 1154, 954, 786, 698, 545 cm$^{-1}$. MS (FAB): m/z (%) 542 (MH$^+$, 46).

EXAMPLE 23 tert-Butyl (1R)-2-((2S)-2-{[(2-amino-5,6,7,8-tetrahydro-6-quinazolinyl)amino]carbonyl}pyrrolidinyl)-1-benzhydryl-2-oxoethylcarbamate

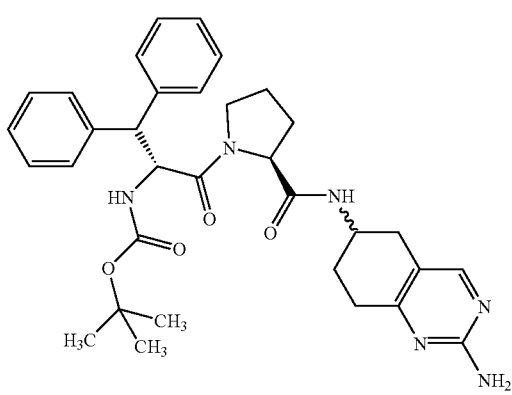

The title compound was prepared from Boc-D-3,3-(Ph)$_2$-Ala-L-Pro-OH and 2,6-diamino-5,6,7,8-tetrahydroquinazoline using the procedure of EXAMPLE 6, and was obtained as a white solid.

Yield: 81% Melting point: 128–131° C. IR (KBr): v=3414, 2974, 1639, 1548, 1452, 1366, 1253, 1166, 1017, 864, 755, 701, 604 cm$^{-1}$. MS (FAB): m/z (%) 585 (MH$^+$, 94).

EXAMPLE 24

(2S)-1-[(2R)-2-Amino-3,3-diphenylpropanoyl]-N-(2-amino-5,6,7,8-tetrahydro-6-quinazolinyl)-2-pyrrolidinecarboxamide dihydrochloride

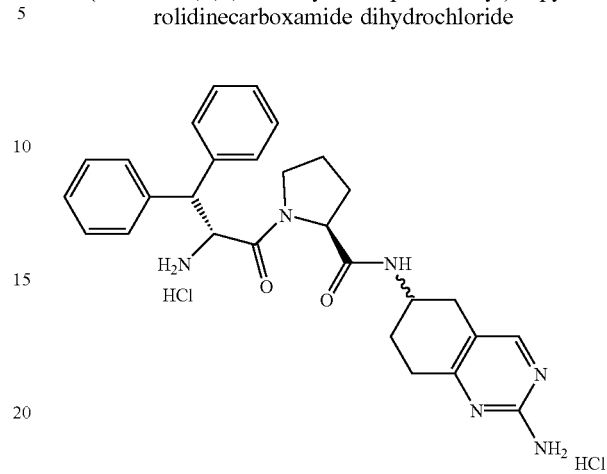

The title compound was prepared from tert-butyl (1R)-2-((2S)-2-{[(2-amino-5,6,7,8-tetrahydro-6-quinazolinyl)amino]carbonyl}pyrrolidinyl)-1-benzhydryl-2-oxoethylcarbamate using the procedure of EXAMPLE 8, and was obtained as a white solid.

Yield: 86% Melting point: 199–202° C. IR (KBr): v=3274, 1655, 1527, 1449, 1350, 1244, 1102, 917, 755, 704, 595 cm$^{-1}$. MS (FAB): m/z (%) 485 (MH$^+$, 100).

EXAMPLE 25 tert-Butyl (1R)-2-((2S)-2-{[(2-amino-4,5,6,7-tetrahydro-1,3-benzothiazol-6-yl)amino]carbonyl}pyrrolidinyl)-1-benzyl-2oxoethylcarbamate

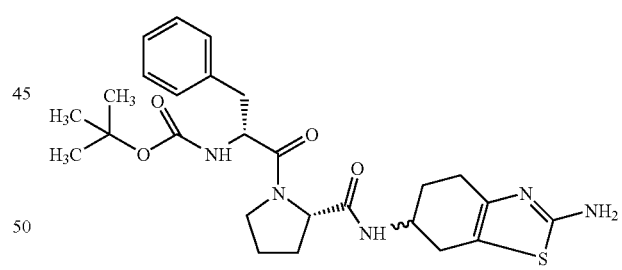

To the solution of Boc-D-Phe-L-Pro-OH (580 mg, 1.60 mmol) and 4,5,6,7-tetrahydro-1,3-benzothiazole-2,6-diamine dihydrobromide (482 mg, 1.46 mmol) in 3.7 mL of N,N-dimethylformamide was added HOBt (247 mg, 1.60 mmol). N-Methylmorpholine was used to set pH of the solution to 8 and EDC (313 mg, 1.60 mmol) was added. The reaction mixture was stirred overnight, the solvent was evaporated in vacuo and the residue partitioned between EtOAc and saturated solution of NaHCO$_3$. Organic layer was washed with brine dried with MgSO$_4$, filtered and the solvent was evaporated under reduced pressure. The crude product was purified with column chromatography (silicagel, CHCl$_3$/MeOH=9/1) to yield 480 mg of faint brown crystalline solid (64%).

Melting point: 120–123° C. IR (KBr): ν=3418, 2975, 1646, 1523, 1448, 1367, 1252, 1167, 860, 752, 702 cm$^{-1}$. MS (FAB): m/z (%) 514 (MH$^+$, 59/2.50), 70 (100).

371 (100). MS (FAB): m/z (%) 568 (MH$^+$, 100). MS (HR):calcd.  $C_{28}H_{33}N_5O_4S_2$: 567.197399.  found 567.195929.

EXAMPLE 26

(2S)-1-[(2R)-2-Amino-3-phenylpropanoyl]-N-(2-amino-4,5,6,7-tetrahydro-1,3-benzothiazol-6-yl)-2-pyrrolidinecarboxamide dihydrochloride

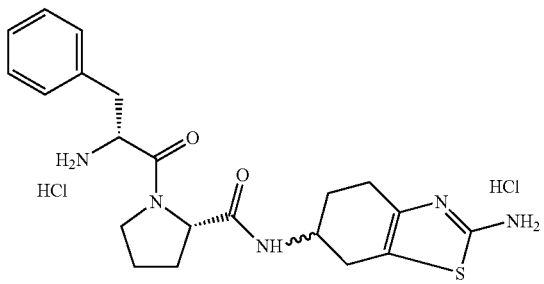

HCl gas was bubbled 50 minutes through a solution of N-(2-amino-4,5,6,7-tetrahydro-1,3-benzothiazol-6yl)-N'-Boc-D-phenylalanyl-L-prolinamide (360 mg, 0.70 mmol) in 10 mL of anhydrous acetic acid at room temperature. Acetic acid was evaporated under reduced pressure and the residue was triturated several times with diethyl ether to yield 280 mg of the title compound as a faint yellow solid (82%).

Melting point: 225–228° C. IR (KBr): ν=3418, 2970, 1643, 1538, 1454, 1361, 1202, 762, 704 cm$^{-1}$. MS (FAB): m/z (%) 414 (MH$^+$, 100).

EXAMPLE 28

(2S)-N-(2-Amino-4,5,6,7-tetrahydro-1,3-benzothiazol-6-yl)-1-{(2R)-2-[(benzylsulfonyl)amino]-3-cyclohexylpropanoyl}-2-pyrrolidinecarboxamide

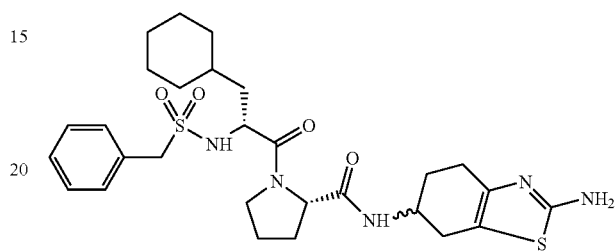

The compound was prepared from N-benzylsulfonyl-(β-cyclohexyl)-D-Ala-L-Pro-OH and 4,5,6,7-tetrahydro-1,3-benzothiazole-2,6-diamine dihydrobromide using the procedure of EXAMPLE 25. The product was obtained as a faint brown crystalline solid.

Yield: 54%. Melting point: 127–130° C. IR (KBr): ν=3357, 2924, 2848, 1638, 1523, 1448, 1311, 1125, 754, 697, 546 cm$^{-1}$. MS: m/z (%) 574 (MH$^+$, 100).

EXAMPLE 27

(2S)-N-(2-amino-4,5,6,7-tetrahydro-1,3-benzothiazol-6-yl)-1-{(2R)-2-[(benzylsulfonyl)amino]-3-phenylpropanoyl}-2-pyrrolidinecarboxamide

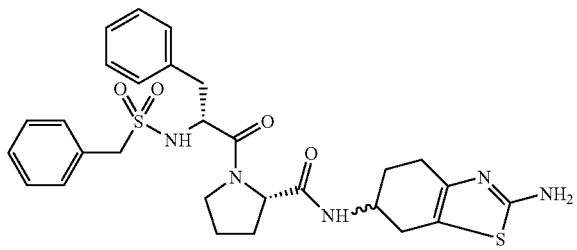

The compound was prepared from N-(benzylsulfonyl)-D-Phe-L-Pro-OH and 4,5,6,7-tetrahydro-1,3-benzothiazole-2,6-diamine dihydrobromide using the procedure of EXAMPLE 25. The product was obtained as a faint yellow solid.

Yield: 49%. Melting point: 126–129° C. IR (KBr): ν=3362, 3192, 2926, 1646, 1522, 1454, 1315, 1152, 1124, 944, 751, 698, 547 cm$^{-1}$. MS (EI): m/z (%) 567 (M$^+$, 27),

EXAMPLE 29

(2S)-N-(2-Amino-4,5,6,7-tetrahydro-1,3-benzothiazol-6-yl)-1-[(2R)-2-[(benzylsulfonyl)amino]-3-(3,4dichlorophenyl)propanoyl]-2-pyrrolidinecarboxamide

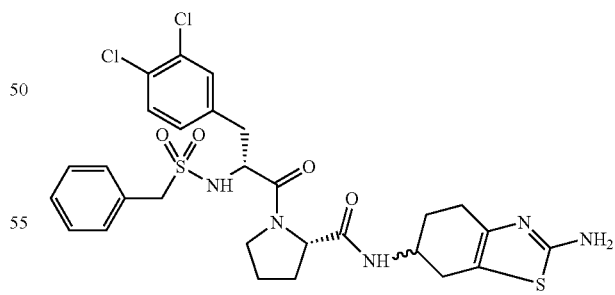

The compound was prepared from N-benzylsulfonyl-(3,4-dichloro)-D-Phe-L-Pro-OH and 4,5,6,7-tetrahydro-1,3-benzothiazole-2,6-diamine dihydrobromide using the procedure of EXAMPLE 25. The product was obtained as a white solid.

Yield: 15%. IR (KBr): ν=3326, 1654, 1522, 1448, 1317, 1152, 1128, 1031, 697, 544 cm$^{-1}$. MS (FAB): m/z (%) 636 (MH$^+$, 100).

EXAMPLE 30

(2S)-N-(2-Amino-4,5,6,7-tetrahydro-1,3-benzothiazol-6-yl)-1-{(2R)-2-[(2-naphthylsulfonyl)amino]-3-phenylpropanoyl}-2-pyrrolidinecarboxamide

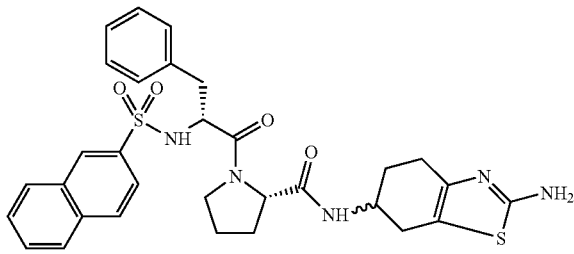

To a solution of (2S)-1-[(2R)-2-Amino-3-phenylpropanoyl]-N-(2-amino-4,5,6,7-tetrahydro-1,3-benzothiazol-6-yl)-2-pyrrolidinecarboxamide dihydrochloride (0.38 mmol, 185 mg) in 6 mL of dichloromethane under argon atmosphere was added 2-naphthalenesulfonyl chloride (0.38 mmol, 84 mg) and then triethylamine (1.52 mmol, 0.21 mL). The mixture was stirred at 0° C. for 1 hour and then overnight at room temperature. Dichloromethane was evaporated, the residue dissolved in ethyl acetate, dichloromethane was added, whereupon the solution was extracted with water, washed with saturated solution of NaHCO$_3$ and with brine. Organic phase was dried over MgSO$_4$, filtered and evaporated under reduced pressure. The product was purified by column chromatography on silica gel using CHCl$_3$/MeOH=9/1 as eluant to yield 70 mg of almost white solid (31%).

Melting point: 128–131° C. IR (KBr): ν=3363, 1637, 1522, 1438, 1308, 1153, 1074, 962, 861, 816, 750, 656, 547, 479 cm$^{-1}$. MS (FAB): m/z (%) 604 (MH$^+$, 100).

EXAMPLE 31

(2R)-N-{2-[(2-Amino-4,5,6,7-tetrahydro-1,3-benzothiazol-6-yl)amino]-2-oxoethyl}-2-[(benzylsulfonyl)amino]3-phenylpropanamide

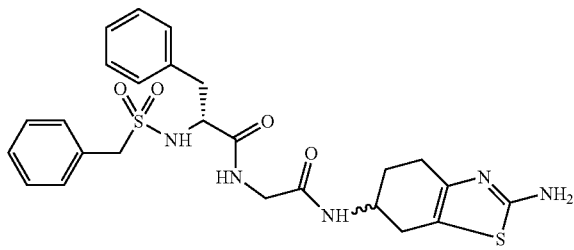

The title compound was prepared from N-benzylsulfonyl)-D-Phe-Gly-OH and 4,5,6,7-tetrahydro-1,3-benzothiazol-2,6-diamine dihydrobromide according to the procedure of EXAMPLE 25, and was obtained as a white solid.

Yield: 37%. Melting point: 119–122° C. IR (KBr): ν=3346, 2926, 1655, 1522, 1455, 1371, 1314, 1233, 1126, 956, 750, 698, 543, 487 cm$^{-1}$. MS (FAB): m/z (%) 528 (MH$^+$, 88), 91 (100).

EXAMPLE 32

(2R)-N-{(1S)-2-[(2-Amino-4,5,6,7-tetrahydro-1,3-benzothiazol-6-yl)amino]-1-methyl-2-oxoethyl}-2-[(benzylsulfonyl)amino]-3-phenylpropanamide

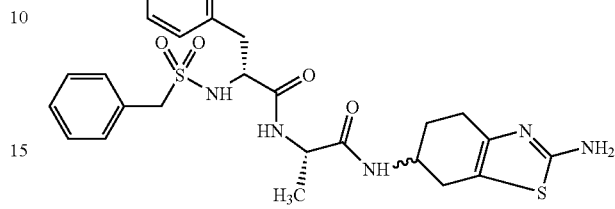

The title compound was prepared from N-(benzylsulfonyl)-D-Phe-L-Ala-OH and 4,5,6,7-tetrahydro-1,3-benzothiazole-2,6-diamine dihydrobromide according to the procedure of EXAMPLE 25, and was obtained as a white solid.

Yield: 37%. Melting point: 122–125° C. IR (KBr): ν=3314, 3200, 2929, 1654, 1523, 1455, 1371, 1315, 1231, 1152, 1126, 952, 750, 698, 545 cm$^{-1}$. MS (FAB): m/z (%) 542 (MH$^+$, 100).

EXAMPLE 33

(2S)-N-(2-Amino-4,5,6,7-tetrahydro-1,3-benzothiazol-6-yl)-1-[2-(tritylamino)acetyl]-2-pyrrolidinecarboxamide

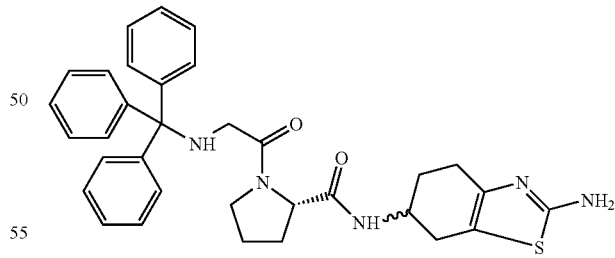

The title compound was prepared from (2S)-1-[2-(Tritylamino)acetyl]-2-pyrrolidinecarboxylic acid and 4,5,6,7-tetrahydro-1,3-benzothiazol-2,6-diamine dihydrobromide according to the procedure described in EXAMPLE 25, and was obtained as a faint yellow crystalline solid.

Yield: 36%. Melting point: 125–128° C. IR (KBr): ν=3410, 2926, 1660, 1640, 1529, 1444, 1411, 1306, 1206, 1031, 901, 748, 104, 535 cm$^{-1}$. MS (FAB): m/z (%) 566 (MH$^+$, 66/10), 243 (100).

EXAMPLE 34 tert-Butyl (1R)-2-((2S)-2-{[(2-amino-4,5,6,7-tetrahydro-1,3-benzothiazol-6-yl)amino]carbonyl}pyrrolidinyl)-1-(3,4-dichlorobenzyl)-2-oxoethylcarbamate

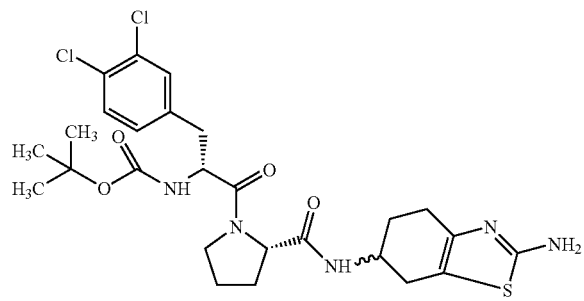

The title compound was prepared from Boc-D-3,4-Cl$_2$-Phe-L-Pro-OH and 4,5,6,7-tetrahydro-1,3-benzothiazole-2,6-diamine dihydrobromide according to the procedure of EXAMPLE 25, and was obtained as a faint yellow solid.

Yield: 77%. Melting point: 116–119° C. IR (KBr): ν=3409, 2977, 1637, 1529, 1444, 1367, 1250, 1165, 1029, 753, 679 cm$^{-1}$. MS (FAB): m/z (%) 582 (MH$^+$, 49), 70 (100).

EXAMPLE 35 tert-Butyl (1S)-2-((2S)-2-{[(2-amino-4,5,6,7-tetrahydro-1,3-benzothiazol-6-yl)amino]carbonyl}pyrrolidinyl)-1-benzhydryl-2-oxoethylcarbamate

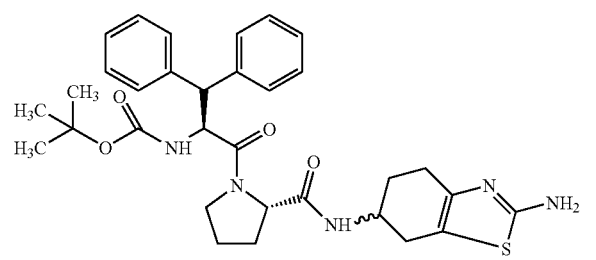

The title compound was prepared from Boc-L-3,3-(Ph)$_2$-Ala-L-Pro-OH and 4,5,6,7-tetrahydro-1,3-benzothiazole-2,6-diamine dihydrobromide according to the procedure described in EXAMPLE 25, and was obtained as a faint yellow solid.

Yield: 62%. Melting point: 127–130° C. IR (KBr): ν=3305, 2977, 1634, 1526, 1443, 1368, 1249, 1165, 1018, 862, 753, 700 cm$^{-1}$. MS (FAB): m/z (%) 590 (MH$^+$, 35), 70 (100).

EXAMPLE 36

(2S)-1-[(2R)-2-amino-3-(3,4-dichlorophenyl)propanoyl]-N-(2-amino-4,5,6,7-tetrahydro-1,3-benzothiazol-6-yl)-2-pyrrolidinecarboxamide dihydrochloride

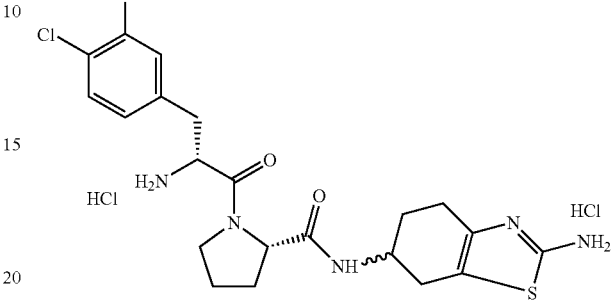

The title compound was prepared from tert-butyl (1R)-2-((2S)-2-{[(2-amino-4,5,6,7-tetrahydro-1,3-benzothiazol-6-yl)amino]carbonyl}pyrrolidinyl)-1-(3,4-dichlorobenzyl)-2-oxoethylcarbamate according to the procedure of EXAMPLE 26. The product was obtained as a faint yellow solid.

Yield: 96%. Melting point: 166–169° C. IR (KBr): ν=2973, 1643, 1469, 1358, 1261, 1132, 1032, 878, 826, 713, 586 cm$^{-1}$. MS (FAB): m/z (%) 482 (MH$^+$, 100).

EXAMPLE 37

(2S)-1-[(2S)-2-amino-3,3-diphenylpropanoyl]-N-(2-amino-4,5,6,7-tetrahydro-1,3-benzothiazol-6-yl)-2-pyrrolidinecarboxamide dihydrochloride

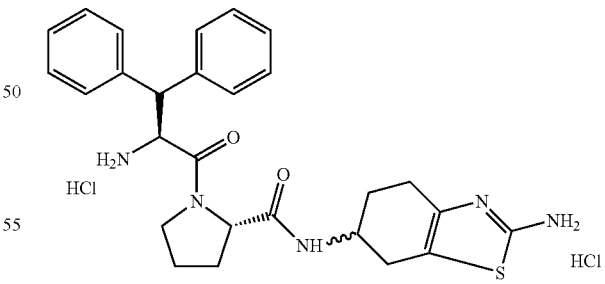

The title compound was prepared from tert-butyl (1S)-2-((2S)-2-{[(2-amino-4,5,6,7-tetrahydro-1,3-benzothiazol-6-yl)amino]carbonyl}pyrrolidinyl)-1-benzhydryl-2-oxoethylcarbamate according to the procedure of EXAMPLE 26. The product was obtained as an almost white solid.

Yield: 97%. Melting point: 155–158° C. IR (KBr): ν=3390, 2974, 1641, 1449, 1347, 1242, 1112, 913, 753, 704 cm$^{-1}$. MS (FAB): m/z (%) 490 (MH$^+$, 73), 149 (100).

EXAMPLE 38

(2S)-N-(2-Amino-1,3-benzothiazol-6-yl)-1-{(2R)-2-[(benzylsulfonyl)amino]-3-phenylpropanoyl}-2-pyrrolidinecarboxamide

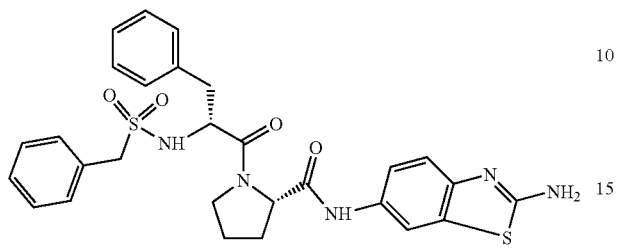

The title compound was prepared from N-(benzylsulfonyl)-D-Phe-OH and (2S)-N-(2-amino-1,3-benzothiazol-6-yl)-2-pyrrolidinecarboxamide dihydrochloride according to the procedure of EXAMPLE 25, and was obtained as a faint yellow crystalline solid Yield: 33%. Melting point: 130–133° C. IR (KBr): ν=3314, 1637, 1526, 1466, 1407, 1307, 1227, 1150, 1123, 934, 819, 748, 698, 544, 488 cm$^{-1}$. MS (FAB): m/z (%) 564 (MH$^+$, 100).

EXAMPLE 39

(2R)-N-{2-[(2-Amino-1,3-benzothiazol-6-yl)amino]-2-oxoethyl}-2-[(benzylsulfonyl)amino]-3-phenylpropanamide

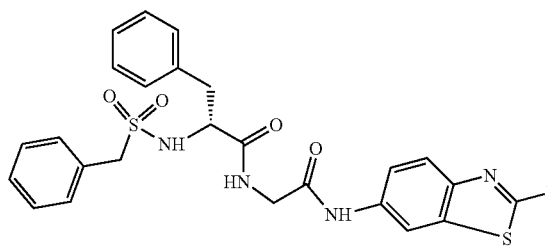

The title compound was prepared from N-benzilsulfonyl)-D-Phe-OH and 2-amino-N-(2-amino-1,3benzothiazol-6-yl) acetamide dihydrochloride essentially according to the procedure of EXAMPLE 25, and was obtained as an intensively yellow coloured solid.

Yield: 29%. Melting point: 127–130° C. IR (KBr): ν=3351, 1639, 1530, 1466, 1408, 1307, 1123, 958, 818, 697, 539 cm$^{-1}$. MS: m/z (%) 524 (MH$^+$, 100).

EXAMPLE 40

Phenylmethyl (2S)-2-{[(4amino-6-quinazolinyl)amino]carbonyl}-1-pyrrolidinecarboxylate

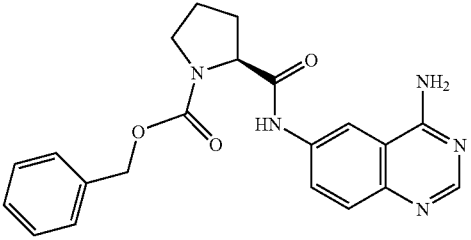

To a cooled solution of Z-L-Pro-OH (1.61 g, 7.5 mmol) in 6 mL of N,N-dimethylformamide, ethylcloroformate (0.79 mL, 8.25 mmol) and trietylamine (1.15 mL, 8.25 mmol) were added. After the mixed anhydride was formed 4,6-quinazolinediamine (1.2 g, 7.5 mmol) was added and the solution was stirred for 12 hours. N,N-dimethylformamide was evaporated in vacuo. The residual brownish oil was purified with column chromatography using CHCl$_3$/MeOH (9/1) as eluant.

Yield: 47% $^1$H-NMR (300 MHz, DMSO-d$_6$): δ 1.93–1.97; 2.09–2.27 (2*m, 4H, ProCH$_2$β, ProCH$_2$γ), 3.46–3.52 (m, 2H, ProCH$_2$δ), 4.40–4.46 (m, 1H, ProCHα), 4.95–5.15 (m(2*AB-system), 2H, (Z)PhCH$_2$), 7.07–7.15; 7.23–7.40; 7.50–7.80; 8.30–8.39 (4*m, 11H, (Z)PhCH-(2-6), QuinCH-(2,5,7,8), QuinNH$_2$-4), 10.28 (s, 1H, Quin-NHCO).

* cis/trans conformers

Analysis for C$_{21}$H$_{21}$N$_5$O$_3$*2.25H$_2$O: Calcd.: 58.40%; C, 5.38%; H, 16.22%; N. Found: 58.29%; C, 5.88%; H, 15.98%; N.

EXAMPLE 41

(2S)-N-(4-Amino-6-quinazolinyl)-2-pyrrolidinecarboxamide

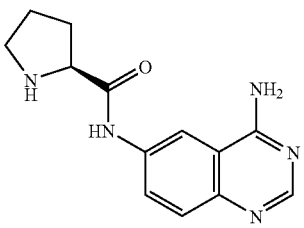

Phenylmethyl(2S)-2-{[(4-amino-6-quinazolinyl)amino]carbonyl}-1-pyrrolidinecarboxylate (1.97 g, 5 mmol) was dissolved in 100 mL of methanol. 10% Pd—C (0.2 g) was added and the mixture was hydrogenated at ca. 40 psi (2.76 bar). After the catalyst was filtered off the solvent was evaporated to give yellowish oil.

MS (EI): m/z (%) 257 (M$^+$, 50), 70 (100). MS (HR): Calcd. C$_{13}$H$_{15}$N$_5$O: 257.27660. Found: 257.127060. $^1$H-NMR (300 MHz, DMSO-d$_6$): δ 1.60–1.70; 1.80–1.90; 2.00–2.15 (3*m, 4H, ProCH$_2$β, ProCH$_2$γ), 2.90–3.00; 3.45–3.55 (2*m, 2H, ProCH$_2$δ), 3.70–3.80 (m, 1H, ProCHα), 7.37 (s, 2H, QuinNH$_2$-4), 7.63 (d, 1H, J=9.0 Hz, QuinCH-8), 8.12 (dd, 1H, J$_1$=9.0 Hz, J$_2$=2.2 Hz, QuinCH-7), 8.24 (d, 1H, J=2.2 Hz, QuinCH-5), 8.31 (s, 1H, QuinCH- 2), 10.18 (s, 1H, QuinNHCO). Analysis for $C_{13}H_{15}N_5O$* $H_2O$*MeOH: Calcd.: 54.71%; C, 6.89%; H, 22.79%; N. Found: 54.72%; C, 6.77%; H, 22.79%; N.

EXAMPLE 42

(2S)-N-(4-amino-6-quinazolinyl)-1-{2-[(triphenylmethyl)amino]acetyl}-2-pyrrolidinecarboxamide

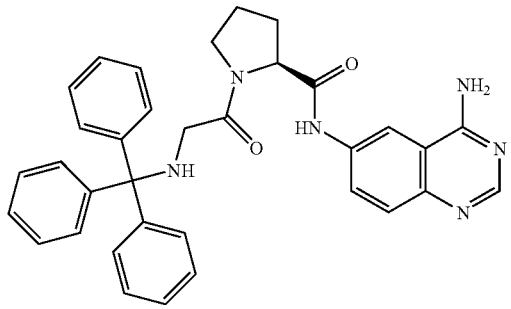

N-Tritylglycine (1.58 g, 5.0 mmol) and (2S)-N-(4-amino-6-quinazolinyl)-2-pyrrolidinecarboxamide (1.15 g, 4.5 mmol) were dissolved in 11 mL N,N-dimethylformamide and cooled to 0° C. HOBt (0.770 g, 5.0 mmol) was added and pH was set to 8 with N-methylmorpholine. After 10 minutes EDC (0.978 g, 5.0 mmol) was added and the mixture was stirred for 12 hours. The solvent was evaporated and the crude product was purified with column chromatography using chloroform/methanol (9/1) as eluant.

Yield: 42%. MP >250° C. MS (EI): m/z (%) 557 (MH$^+$, 25/10), 243 (100). MS (FAB): m/z (%) 556 (M$^+$, 20/400). $^1$H-NMR* (300 MHz, DMSO-$d_6$): δ 1.75–2.05 (2*m, 4H, ProCH$_2$β, ProCH$_2$γ), 2.85–3.20; 3.40–3.50; 4.20–4.45 (7*m, 5H, ProCH$_2$δ, ProCHα, GlyCH$_2$), 7.00–7.40 (4*m, 16H, 3*(tritil)PhCH-(2–6), QuinCH-5), 7.50–7.66 (2*s+2*d (J=9.0 Hz), 3H, QuinCH-8, QuinNH$_2$-4), 7.73 (dd, 1H, J$_1$=9.0 Hz, J$_2$=2.2 Hz, QuinCH-7), 8.28(8.30) (2*s, 1H, QuinCH-2), 8.33–8.35(m, 1H, GlyNH), 10.17(10.19) (2*s, 1H, QuinNHCO).

* cis/trans conformers

EXAMPLE 43

1,1-Dimethylethyl 2-[(4-amino-6-quinazolinyl)amino]-2-oxoethylcarbamate

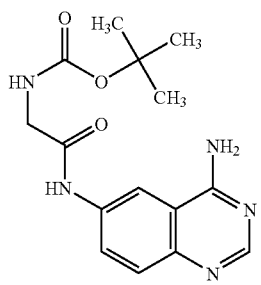

The product was prepared from BOC-Gly-OH and 4,6-quinazolinediamine using the procedure described in EXAMPLE 40.

Yield: 50%. IR (KBr): ν=3336, 2977, 1700, 1575, 1540, 1510, 1367, 1164 cm$^{-1}$. MS (EI): m/z (%) 317 (M$^+$, 25), 160 (100). MS (FAB): m/z (%) 318 (MH$^+$, 70). MS (HR): Calcd. $C_{15}H_{19}N_5O_3$: 317.148790. Found: 317.148909. $^1$H-NMR (300 MHz, DMSO-$d_6$): δ 1.38–1.40 (2*s, 9H, (CH$_3$)$_3$), 3.78 (d, 2H, J=6.2 Hz, GlyCH$_2$), 7.07 (t, 1H, J=6.2 Hz, GlyNH), 7.60 (s, 2H, QuinNH$_2$-4), 7.64 (d, 1H, J=9.0 Hz, QuinCH-8), 7.75–7.80 (dd, 1H, QuinCH-7), 8.31 (s, 1H, QuinCH-2), 8.33 (d, 1H, J=1.7 Hz, QuinCH-5), 10.11 (s, 1H, QuinNHCO).

EXAMPLE 44

2-Amino-N-(4-amino-6-quinazolinyl)acetamide dihydrochloride

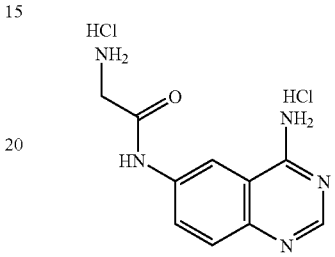

1,1-Dimethylethyl 2-[(4-amino-6-quinazolinyl)amino]-2-oxoethylcarbamate (0.5 g, 1.58 mmol) was dissolved in 30 mL acetic acid and HCl gas was passed through the solution till thin laser chromatography indicated a quantitative conversion. Acetic acid was evaporated in vacuo and the crude product triturated with ether to give a quantitative yield of a pale yellow solid.

IR (KBr): ν=3458, 1646, 1490, 1244 cm$^{-1}$. MS (FAB): m/z (%) 218 (MH$^+$, 100). $^1$H-NMR (300 MHz, DMSO-$d_6$): δ 3.90 (d, 2H, J=5 Hz, GlyCH$_2$), 7.90 (d, 1H, J=9.0 Hz, QuinCH-8), 8.14 (dd, 1H, J$_1$=9.0 Hz, J$_2$=1.9 Hz, QuinCH-7), 8.39 (s, 2H, QuinNH$_2$-4), 8.33 (d, 1H, J=1.9 Hz, QuinCH-5), 8.76 (s, 1H, QuinCH-2), 9.70 (s, 1H, GlyNH), 9.93 (s, 1H, GlyNH), 11.45 (s, 1H, QuinNHCO).

EXAMPLE 45

2,4,6-Quinazolinetriamine

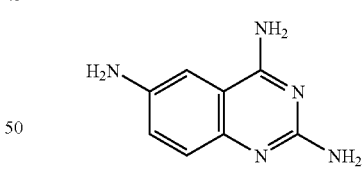

To a solution of guanidine carbonate (0.9 g, 5.0 mmol) in 30 mL methanol was added sodium (0.24 g, 10.4 mmol) and the mixture was heated under reflux for 30 minutes. The precipitated sodium carbonate was filtered off and washed with methanol. 2-Amino-5-nitrobenzonitrile (0.88 g, 5.4 mmol) was added to the methanolic solution which was then heated under reflux for additional 24 hours. The solvent was evaporated and the crude 6-nitro-2,4-quinazolinediamine subjected to catalytic hydrogenation as described in EXAMPLE 41.

Yield: 45%. MP: >250° C. MS: m/z (%) 175(MH$^+$, 100). $^1$H-NMR (300 MHz, DMSO-$d_6$): δ 4.75 (s, 1H, QuinNH$_2$-2), 5.44 (s, 2H, QuinNH$_2$-6), 6.83 (s, 2H, QuinNH$_2$-4), 6.95–7.03 (m, 3H, QuinCH-(5,7,8)).

EXAMPLE 46

1,1-Dimethylethyl (1R)-2-({2-[(2,4-diamino-6-quinazolinyl)amino]-2-oxoethyl}amino)-2-oxo-1-phenylmethyl)ethylcarbamate

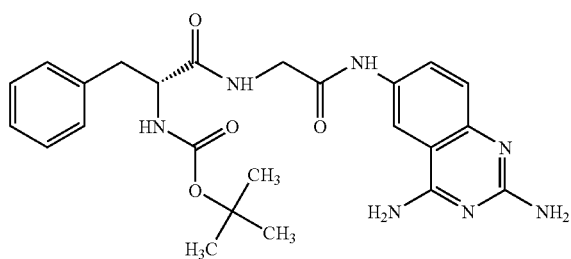

The product was prepared by condensation of BOC-D-Phe-OH and 2-amino-N-(2,4-diamino-6-quinazolinyl)acetamide using the procedue described in EXAMPLE 42.

Yield: 40% IR (KBr): ν=3458, 1648, 1570, 1389, 1242 cm$^{-1}$. MS (FAB): m/z (%) 480 (MH$^+$, 65). $^1$H-NMR (300 MHz, DMSO-d$_6$): δ 1.20–1.31 (m, 9H, (CH$_3$)$_3$), 2.73–3.31 (m(Abx), 2H, PheCH$_2$), 3.95 (d, 2H, J=5.2 Hz, GlyCH$_2$), 4.16–4.23 (m, 1H, PheCH), 7.00–7.72 (3*m, 9H, PheNH, QuinCH-(5,7,8), (Phe)PhCH-(2–6)), 8.38–8.42 (m, 1H, GlyNH), 10.11 (s, 1H, QuinNHCO).

EXAMPLE 47

(2R)-2-Amino-N-{2-[(2,4-diamino-6-quinazolinyl)amino]-2-oxoethyl}-3-phenylpropanamide hydrochloride

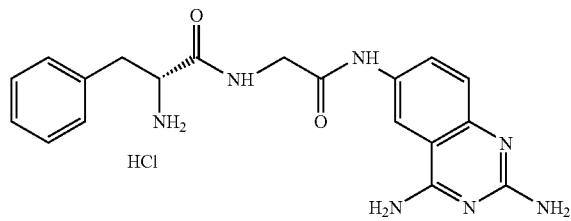

The product was prepared from 1,1-dimethylethyl (1R)-2-({2-[(2,4-diamino-6-quinazolinyl)-amino]-2-oxoethyl}amino)-2-oxo-1-(phenylmethyl)ethylcarbamate using the procedue described in EXAMPLE 44.

IR (KBr): ν=3382, 3085, 1703, 1601, 1489, 1394, 1311, 1219 cm$^{-1}$. MS (FAB): m/z (%) 380 (MH$^+$, 80). $^1$H-NMR (300 MHz, DMSO-d$_6$): δ 3.03–3.23 (m(Abx), 2H, PheCH$_2$); 3.99–4.06 (m, 2H, GlyCH$_2$), 4.13–4.18 (m, 1H, PheCH), 7.27–7.33 (m, 5H, (Phe)PhCH-($_{2-6}$)), 7.44 (d, 1H, J=9.0 Hz, QuinCH-8), 7.70(s, 2H, QuinNH$_2$-4), 7.88–7.91 (m, 1H, QuinCH-7), 8.39 (m, 1H, QuinCH-5), 8.77 (s, 2H, QuinNH$_2$-2), 9.07–9.11 (m, 1H, GlyNH), 10.45 (s, 1H, QuinNHCO).

EXAMPLE 48

Phenylmethyl(2S)-2-{[(2,4-diamino-6-quinazolinyl)amino]carbonyl}-1-pyrrolidinecarboxylate

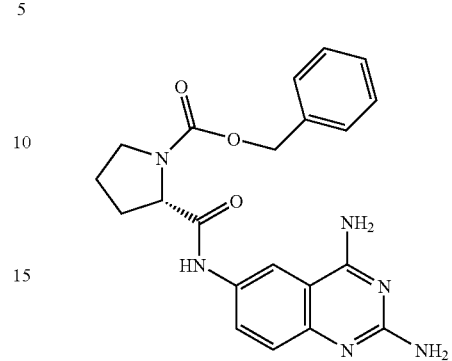

The product was prepared from 2,4,6-quinazolinetriamine and benzyl chloroformate according to the procedure described in EXAMPLE 40.

IR (KBr): ν=3418, 1654, 1560, 1425, 1358, 697 cm$^{-1}$. MS (EI): m/z (%) 406 (M$^+$, 35), 91 (100). MS (FAB): m/z (%) 407 (MH$^+$, 100).

EXAMPLE 49

N-(2,4-Diamino-6-quinazolinyl)-2-[(2S)-1-((2R)-3-phenyl-2-{[(phenylmethyl)sulfonyl]amino}propanoyl)pyrrolidinyl]acetamide

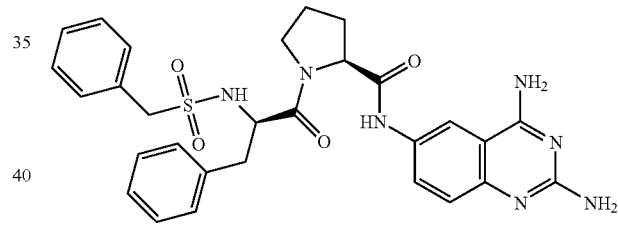

Prepared from (2R)-2-[(benzylsulfonyl)amino]-3-phenylpropanoic acid and (2S)-N-(2,4-diamino-6-quinazolinyl)-2-pyrrolidinecarboxamide using the procedure described in EXAMPLE 42.

MS (FAB): m/z (%) 574 (MH$^+$, 100). $^1$H-NMR* (300 MHz, DMSO-d$_6$): δ 1.50–2.60 (6*m, 4H, 1-ProCH$_2$γ(1.6), 2-ProCH$_2$γ(1.9), 3-ProCH$_2$β(1.9), 4-ProCH$_2$β(2.2), 5-ProCH$_2$γ(2.3), 6-ProCH$_2$β(2.6)), 2.70–3.50 (5*m (2*AB$_{system}$), 4H, 7-PheCH$_2$(2.7), 8-PheCH$_2$(2.8), 9-PheCH$_2$(2.8), 10-ProCH$_2$δ(2.9), 11-PheCH$_2$(3.0), 12-ProCH$_2$δ(3.5)), 3.6–4.9 (9*m (3*AB$_{system}$), 4H, CH$_2$SO$_2$(1)(3.6–3.8), 13-PheCH(3.9), 14-PheCH(4.0), CH$_2$SO$_2$(2)(4.0–4.1), 15-ProCHα(4.1), CH$_2$SO$_2$(3)(4.1–4.3), 16-PheCH(4.2), 17-ProCHα(4.3), 18-ProCHα(4.9)), 6.65 (bs, 2H, QuinNH$_2$-2), 7.15–7.83 (3*m, 11H, (Phe)PhCH-(2–6), (BzSO$_2$)PhCH-(2–6), PheNH), 7.16 (d, $^-$1H, J=9 Hz, QuinCH-8)#, 7.59 (dd, ~1H, J$_1$=9 Hz, J$_2$=2 Hz, QuinCH-7)#, 7.65 (bs, 2H, QuinNH$_2$-4), 8.11(8.39)# (d, 1H, J=2 Hz, QuinCH-5), 9.89(10.53)# (s, 1H, QuinNHCO).

* cis/trans conformers $^{13}$C NMR (75 MHz, DMSO-d$_6$): δ 24.9, 30.1, 47.6, 56.7, 56.9, 58.9, 59.4, 60.9, 110.3, 111.2, 115.2, 119.5, 124.5, 127.1, 127.7, 128.7, 128.9, 129.1, 130.3, 130.4, 131.0, 131.5, 131.6,131.8, 133.7, 137.4,138.7, 158.1, 163.3, 170.7, 171.0. DEPT135 (75 MHz, DMSO-$d_6$): δ $CH_2$: 24.9, 30.1, 47.6, 58.9, 59.4; CH: 56.7, 60.9, 115.2, 127.1, 127.7, 128.7, 128.9, 129.1, 130.3, 130.4, 131.0, 131.5, 131.6, 131.8.
HMQC-Selected Correlations.

| Atom | $^{13}$C [ppm] | $^1$H correlation [ppm] |
|---|---|---|
| ProCγ | 24.9 | 1.6 (1-ProGH$_2$γ), 1.9 (2-ProCH$_2$γ) |
| ProCβ | 30.1 | 1.9 (3-ProCH$_2$β) |
| PheCH$_2$C | 39.0 | 2.7 (7-PheCH$_2$), 2.8 (9-PheCH$_2$), 3.0 (11-PheCH$_2$) |
| ProCδ | 47.6 | 2.9 (10-ProCH$_2$δ), 3.5 (12-ProCH$_2$δ) |
| PheCH | 56.7 | 4.2 (15-PheCH) |
| CH$_2$SO$_2$C | 58.9 | 3.6(3.8)$^+$ (CH$_2$SO$_2$(1)), 4.0(4.1)$^+$ (CH$_2$SO$_2$(2)) |
|  | 59.4 | 4.1 (4.3)$^+$ (CH$_2$SO$_2$(3)) |
| ProCα | 60.9 | 4.3 (17-ProCHα), 4.9 (18-ProCHα) |

$^+$AB$_{system}$

COSYGS-Selected Correlations.

| Atom | δ [ppm] | $^1$H correlation [ppm] |
|---|---|---|
| 1-ProCH$_2$γ | 1.6 | 1.9(2-ProCH$_2$γ), 2.9(10-ProCH$_2$δ), 3.5(12-ProCH$_2$δ) |
| 2-ProCH$_2$γ | 1.9 | 2.9(10-ProCH$_2$δ), 3.5(12-ProCH$_2$δ) |
| 3-ProCH$_2$β | 1.9 | 4.1(15-ProCH$_2$β), 4.3(17-ProCβ) |
| 4-ProCH$_2$β | 2.2 | 2.6(6-ProCH$_2$β), 4.9(18-ProCHβ) |
| 5-ProCH$_2$γ | 2.3 | 3.5(12-ProCH$_2$δ) |
| 6-ProCH$_2$β | 2.6 | 4.9(17-ProCHα) |
| 7-PheCH$_2$ | 2.7 | 2.8(8-PheCH$_2$), 4.0(14-PheCH) |
| 8-PheCH$_2$ | 2.8 | 4.0(14-PheCH) |
| 9-PheCH$_2$ | 2.8 | 3.9(13-PheCH), 4.2(15-PheCH) |
| 10-ProCH$_2$δ | 2.9 | 3.5(12-ProCH$_2$δ) |
| 11-PheCH$_2$ | 3.0 | 3.9(13-PheCH) |
| QuinCH-8 | 7.2 | 7.6(QuinArCH-7) |
| QuinCH-7 | 7.6 | 8.1(QuinArCH-5) |
| QuinCH-7 | 7.7 | 8.3(QuinArCH-5) |

EXAMPLE 50

N-(4-amino-6-quinazolinyl)-2-((2S)-1-{(2R)-2-[(benzylsulfonyl)amino]-3-phenylpropanoyl}pyrrolidinyl)acetamide

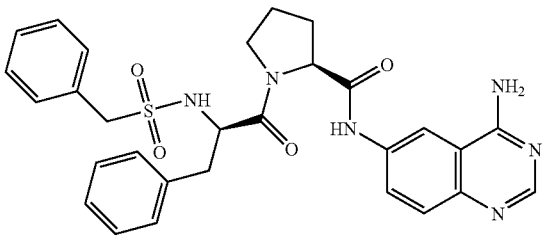

Prepared from (2R)-2-[(benzylsulfonyl)amino]-3-phenylpropanoic acid and (2S)-N-(4-amino-6-quinazolinyl)-2-pyrrolidinecarboxamide using the procedure described in EXAMPLE 42.

MS (FAB): m/z (%) 559 (MH$^+$, 100). $^1$H-NMR* (300 MHz, DMSO-$d_6$): δ1.55–1.65 (m, 1H, 1-ProCH$_2$γ(1.6)), 1.85–1.95 (m, 3H, 2-ProCH$_2$γ(1.9), ProCH$_2$β), 2.85–3.10 (m, 3H, PheCH$_2$, 1-ProCH$_2$δ(3.0)), 3.55–4.35 (3*m(2* AB$_{system}$), 4H, 2-ProCH$_2$δ(3.6), CH$_2$SO$_2$(1)(3.6–3.8), CH$_2$SO$_2$(2)(4.22 (AB$_{system}$, $J_{AB}$=13.7), 1-PheCH(4.0), 2-PheCH(4.3)), 4.35–4.90 (m, 1H, 1-ProCHα(4.3), 2-ProCHα(4.9)), 6.90–8.48 (5*m, 11H, (Phe)PhCH-(2–6), (BzSO$_2$)PhCH-(2–6), PheNH), 7.47 (bs, 2H, QuinNH$_2$-4), 7.54(7.71)# (d, 1H, J=9 Hz, QuinCH-8), 7.77 (dd, 1H, $J_1$=9 Hz, $J_2$=2.1 Hz, QuinCH-7)#, 8.25(8.48)# (d, 1H, J=2.1 Hz, QuinCH-5), 8.28 (s, 1H, QuinCH-2), 10.08(10.70)# (s, 1H, QuinNHCO).

* cis/trans conformers $^{13}$C NMR (75 MHz, DMSO-$d_6$): δ25.0, 30.1, 39.1, 47.6, 56.7, 59.5, 58.9, 60.9, 65.8 113.3, 115.2, 127.6, 127.7, 128.7, 128.8, 129.0, 129.1, 130.3, 131.0, 131.5, 131.5, 131.8, 136.5, 137.4, 147.2, 155.1, 162.1, 170.7, 171.2. DEPT135 (75 MHz, DMSO-$d_6$): δ CH$_2$: 25.0, 30.1, 39.1, 47.6, 59.4; CH: 56.7, 60.9, 113.3, 127.6, 127.7, 128.7, 128.8, 129.0, 129.1, 130.3, 131.5, 131.8, 155.1.
HMQC-selected correlations.

| Atom | $^{13}$C [ppm] | $^1$H correlation [ppm] |
|---|---|---|
| ProCγ | 25.0 | 1.6(1-ProCH$_2$γ), 1.9(2-ProCH$_2$γ) |
| ProCβ | 30.1 | 1.9(ProCH$_2$β) |
| PheCH$_2$C | 39.1 | 2.8–3.0(PheCH$_2$) |
| ProCδ | 47.6 | 3.0(1-ProCH$_2$δ), 3.6(2-ProCH$_2$δ) |
| PheCH | 56.7 | 4.0(1-PheCH), 4.3(2-PheCH) |
| CH$_2$SO$_2$C | 59.5 | 3.6(3.8)$^+$(CH$_2$SO$_2$(1)), 4.1(4.3)$^+$(CH$_2$SO$_2$(2)) |
| ProCα | 60.9 | 4.3(1-ProCHα), 4.9(2-ProCHα) |

$^+$AB$_{system}$

EXAMPLE 51 tert-Butyl (2S)-2-{[(2-amino-1,3-benzothiazol-6-yl)amino]carbonyl}-1-pyrrolidinecarboxylate

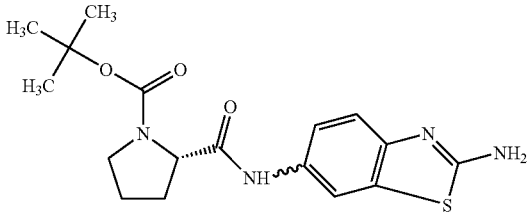

To a cooled solution of Boc-L-Pro-OH (7.5 mmol, 1.61 g) in 6 mL of N,N-dimethylformamide, ethylchloroformate (8.25 mmol, 0.79 mL) and triethylamine (8.25 mmol, 1.15 mL) were added. After the mixed anhydride was formed, 1,3-benzothiazol-2,6-diamine (7.5 mmol, 1.24 g) was added and the solution was stirred on the ice bath for 12 hours. N,N-Dimethylformamide was evaporated in vacuo to give brownish oil, which was triturated with diethyl ether to furnish a brownish solid (2.21 g, 81%).

IR(KBr): ν=3303, 2974, 1672, 1531, 1472, 1411, 1230, 1159, 1124, 816 cm$^{-1}$. MS (FAB): m/z (%) 363 (MH$^+$, 85), (100).

EXAMPLE 52

(2S)-N-(2-amino-1,3-benzothiazol-6-yl)-2-pyrrolidinecarboxamide dihydrochloride

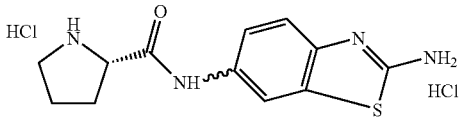

HCl gas was bubbled for 50 minutes through a solution of tert-butyl (2S)-2-{[(2-amino-1,3-benzothiazol-6-yl)amino]carbonyl}-1-pyrrolidinecarboxylate (2.21 g, 6.1 mmol) in 6 mL of anhydrous acetic acid at room temperature. Acetic acid was evaporated under reduced pressure and the residue was triturated several times with diethyl ether and dried above NaOH to yield 1.35 g (54%) of the title compound as brownish solid.

EXAMPLE 53 tert-Butyl 2-[(2-amino-1,3-benzothiazol-6-yl)amino]-2-oxoethylcarbamate

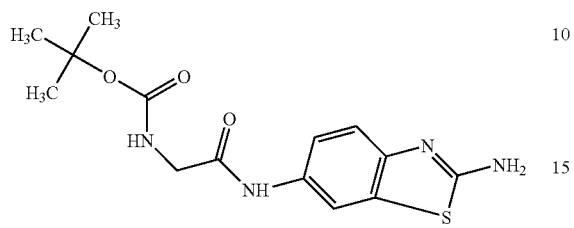

The title compound was prepared from Boc-Gly-OH and 1,3-benzothiazol-2,6-diamine according to the procedure of EXAMPLE 51. The product was obtained as a yellow solid.

Yield: 20%. IR (KBr): ν=3303, 2974, 1672, 1531, 1472, 1411, 1230, 1159, 1124, 816 cm$^{-1}$. MS (FAB): m/z (%) 323 (MH$^+$, 100).

EXAMPLE 54

2-Amino-N-(2-amino-1,3-benzothiazol-6-yl)acetamide dihydrochloride

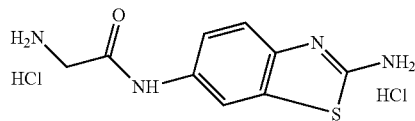

The title compound was prepared from tert-butyl 2-[(2-amino-1,3-benzothiazol-6-yl)amino]-2-oxoethylcarbamate according to the procedure described in EXAMPLE 51; the product was obtained as a faint yellow solid.

Yield: 80%. Melting point: 189–192° C. IR (KBr): ν=3240, 3050, 1697, 1647, 1596, 1560, 1491, 1439, 1318, 1237, 946, 836, 670 cm$^1$. MS (FAB): m/z (%) 223 (MH$^+$, 100).

EXAMPLE 55 tert-Butyl (1R)-1-benzhydryl-2-oxo-2-{(2S)-2-[(4,5,6,7-tetrahydro-2H-indazol-5-ylamino)carbonyl]pyrrolidinyl}ethylcarbamate

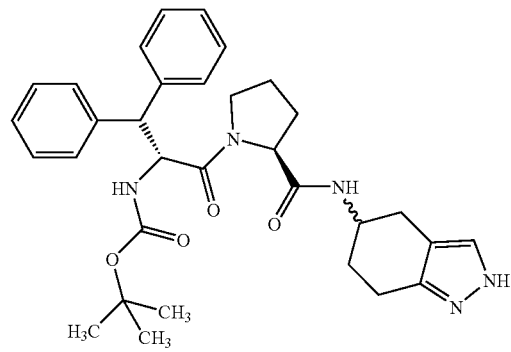

The title compound was prepared from Boc-D-3,3-(Ph)$_2$-Ala-L-Pro-OH and 5-amino-4,5,6,7-tetrahydro-2H-indazole dihydrochloride using the procedure of EXAMPLE 6, and was obtained as a white solid.

Yield: 44% Melting point: 119–122° C. IR (KBr): ν=3292, 2933, 1654, 1528, 1450, 1367, 1252, 1178, 755, 702 cm$^{-1}$. MS (FAB): m/z (%) 557 (MH$^+$, 34).

EXAMPLE 56

(2S)-1-[(2R)-2-Amino-3,3-diphenylpropanoyl]-N-(4,5,6,7-tetrahydro-2H-indazol-5-yl)-2-pyrrolidinecarboxamide dihydrochloride

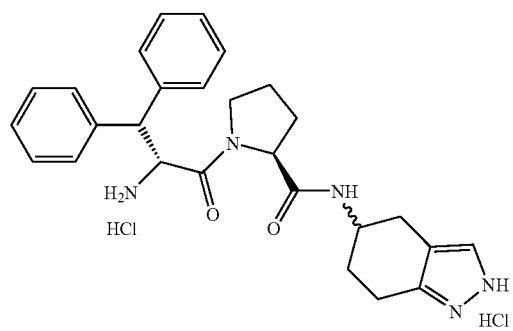

The title compound was prepared from tert-butyl (1R)-1-benzhydryl-2-oxo-2-{(2S)-2-[(4,5,6,7-tetrahydro-2H-indazol-5-ylamino)carbonyl]pyrrolidinyl}ethylcarbamate using the procedure of EXAMPLE 8, and was obtained as a white crystalline solid.

Yield: 99% Melting point: 190–193° C. IR (KBr): ν=2930, 1716, 1652, 1538, 1450, 1345, 1242, 1084, 919, 754, 704 cm$^{-1}$. MS (FAB): m/z (%) 458 (MH$^+$, 100).

EXAMPLE 57

(2S)-N-[(2-Amino-5,6,7,8-tetrahydro-6-quinazolinyl)methyl]-1-{(2R)-2-[(benzylsulfonyl)amino]-3-cyclohexylpropanoyl}-2-pyrrolidinecarboxamide

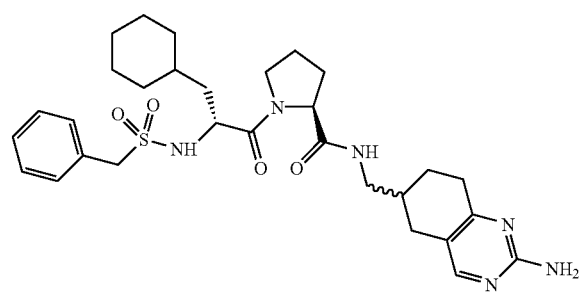

The title compound was prepared from N-(benzylsulfonyl)-D-(ciklohexyl-Ala)-L-Pro-OH and 6-(aminomethyl)-5,6,7,8-tetrahydro-2-quinazolinamine using the procedure of EXAMPLE 6, and was obtained as a white solid.

Yield: 39% Melting point: 118–121° C. IR (KBr): ν3336, 3212, 2923, 2850, 1642, 1557, 1450, 1319, 1146, 752, 698, 545 cm$^{-1}$. MS (FAB): m/z (%) 583 (MH$^+$, 92).

EXAMPLE 58

(2S)-1-{(2R)-2-[(Benzylsulfonyl)amino]-3-cyclohexylpropanoyl}-N-(4,5,6,7-tetrahydro-2H-indazol-5-ylmethyl)-2-pyrrolidinecarboxamide

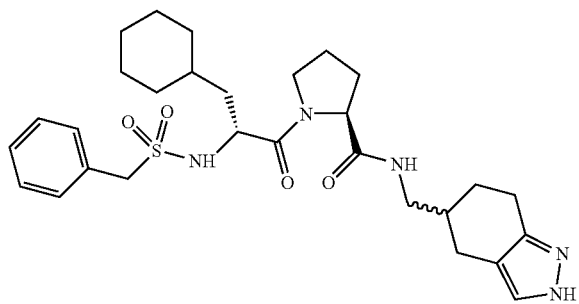

The title compound was prepared from N-(benzylsulfonyl)-D-(cyclohexyl-Ala)-L-Pro-OH and 4,5,6,7-tetrahydro-2H-indazol-5-ylmethanamine dihydrochloride using the procedure of EXAMPLE 6, and was obtained as a white solid.

Yield: 46% Melting point: 100–103° C. IR (KBr): ν3372, 2923, 2850, 1655, 1543, 1448, 1321, 1154, 953, 784, 698, 544 cm$^{-1}$. MS (FAB): m/z (%) 556 (MH$^+$, 35).

EXAMPLE 59 tert-Butyl (1R)-1-(3,4-dichlorobenzyl)-2-oxo-2-((2S)-2-{[(4,5,6,7-tetrahydro-2H-indazol-5-ylmethyl)amino]carbonyl}pyrrolidinyl)ethylcarbamate

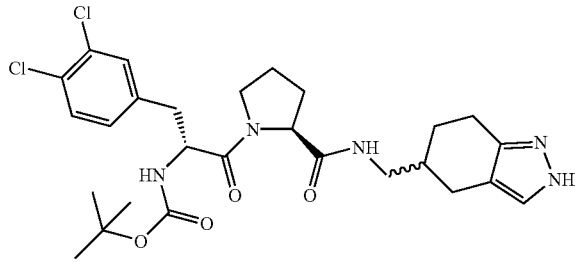

The title compound was prepared from Boc-D-3,4-Cl$_2$-Phe-L-Pro-OH and 4,5,6,7-tetrahydro-2H-indazol-5-ylmethanamine dihydrochloride using the procedure of EXAMPLE 6, and was obtained as a white solid.

Yield: 42% Melting point: 100–103° C. IR (KBr): ν3310, 2930, 1662, 1542, 1441, 1366, 1252, 1167, 956, 754 cm$^{-1}$. MS (FAB): m/z (%) 564 (MH$^+$, 44).

EXAMPLE 60

(2S)-1-[(2R)-2-Amino-3-(3,4-dichlorophenyl)propanoyl]-N-(4,5,6,7-tetrahydro-2H-indazol-5-ylmethyl)-2-pyrrolidinecarboxamide dihydrochloride

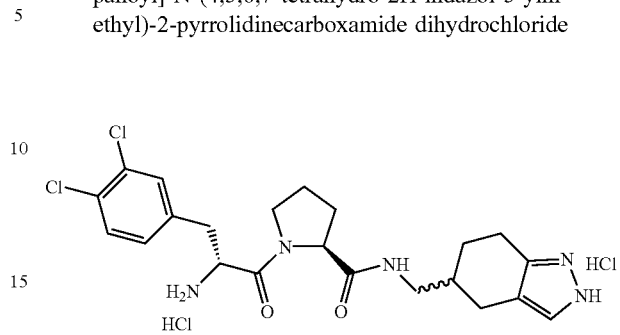

The title compound was prepared from tert-butyl (1R)-1-(3,4-dichlorobenzyl)-2-oxo-2-((2S)-2-{[(4,5,6,7-tetrahydro-2H-indazol-5-ylmethyl)amino]carbonyl}pyrrolidinyl)ethylcarbamate using the procedure of EXAMPLE 8, and was obained as a white crystalline solid.

Yield: 73% Melting point: 145–148° C. IR (KBr): ν=3424, 2930, 1724, 1655, 1468, 1383, 1264, 1131, 1032, 829, 664 cm$^{-1}$. MS (FAB): m/z (%) 464 (MH$^+$, 62).

EXAMPLE 61 tert-Butyl (1R)-2-[(2S)-2-({[(2-amino-5,6,7,8-tetrahydro-6-quinazolinyl)methyl]amino}carbonyl)pyrrolidinyl]1-(3,4dichlorobenzyl)-2-oxoethylcarbamate

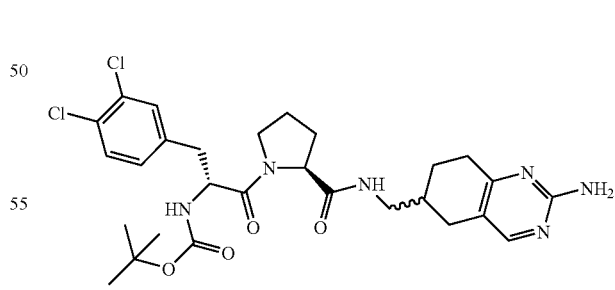

The title compound was prepared from Boc-D-3,4-Cl$_2$-Phe-L-Pro-OH and 6-(aminomethyl)-5,6,7,8-tetrahydro-2-quinazolinamine using the procedure of EXAMPLE 6, and was obtained as a white solid.

Yield: 49% Melting point: 110–113° C. IR (KBr): ν3338, 2978, 1654, 1560, 1471, 1251, 1161, 1030, 752, 682 cm$^{-1}$. MS (FAB): m/z (%) 591 (MH$^+$, 74).

EXAMPLE 62

(2S)-1-[(2R)-2-Amino-3-(3,4-dichlorophenyl)propanoyl]-N-[(2-amino-5,6,7,8-tetrahydro-6-quinazolinyl)methyl]-2-pyrrolidinecarboxamide dihydrochloride

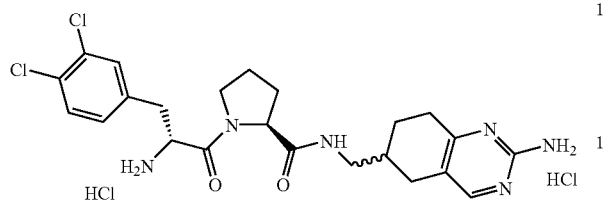

The title compound was prepared from tert-butyl (1R)-2-[(2S)-2-({[(2-amino-5,6,7,8-tetrahydro-6-quinazolinyl)methyl]amino}carbonyl)pyrrolidinyl]-1-(3,4dichlorobenzyl)-2-oxoethylcarbamate using the procedure of EXAMPLE 8, and was obtained as a white crystalline solid.

Yield: 74% Melting point: 169–172° C. IR (KBr): ν3410, 1655, 1545, 1468, 1363, 1205, 1130, 1032, 833, 663 cm$^{-1}$. MS (FAB): m/z (%) 491 (MH$^+$, 50).

EXAMPLE 63

(2S)-1-{(2R)-2-[(Benzylsulfonyl)amino]-3-cyclohexylpropanoyl}-N-(4,5,6,7-tetrahydro-2H-isoindol-5-yl)-2-pyrrolidinecarboxamide

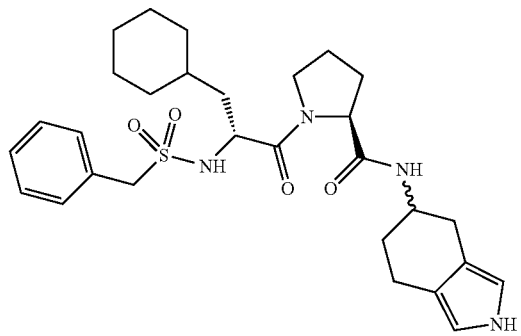

The title compound was prepared from N-(benzylsulfonyl)-D-(cyclohexyl-Ala)-L-Pro-OH and 4,5,6,7-tetrahydro-2H-isoindol-5-amine using the procedure of EXAMPLE 6, and was obtained as a white solid Yield: 37% Melting point: 106–109° C. IR (KBr): ν3385, 2922, 2851, 1654, 1542, 1448, 1320, 1127, 780, 699, 542 cm$^{-1}$. MS (FAB): m/z (%) 541 (MH$^+$, 14)

EXAMPLE 64 tert-Butyl (1R)-1-benzhydryl-2-oxo-2-((2S)-2-{[(4,5,6,7-tetrahydro-2H-indazol-5-ylmethyl)amino]carbonyl}pyrrolidinyl)ethylcarbamate

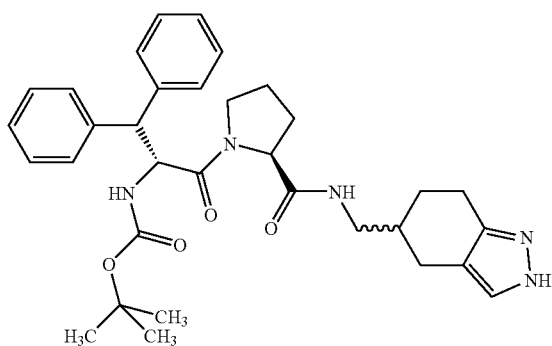

The title compound was prepared from Boc-D-3,3-Ph)$_2$-Ala-L-Pro-OH and 4,5,6,7-tetrahydro-2H-indazol-5-ylmethanamine dihydrochloride using the procedure of EXAMPLE 6, and was obtained as a white solid.

Yield: 74% Melting point: 113–116° C. IR (KBr): ν=3352, 2927, 1654, 1540, 1438, 1367, 1166, 702 cm$^{-1}$. MS (FAB): m/z 572 (%)(MH$^+$, 35).

EXAMPLE 65

(2S)-1-[(2R)-2-Amino-3,3-diphenylpropanoyl]-N-(4,5,6,7-tetrahydro-2H-indazol-5-ylmethyl)-2-pyrrolidinecarboxamide dihydrochloride

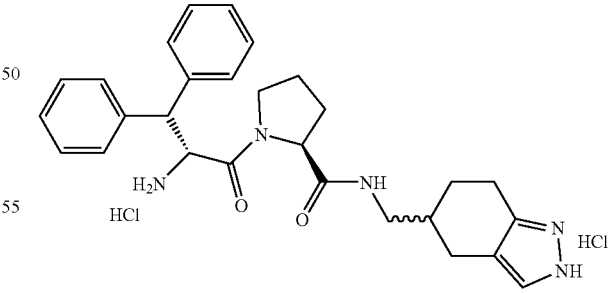

The title compound was prepared from tert-butyl (1R)-1-benzhydryl-2-oxo-2-((2S)-2-{[(4,5,6,7-tetrahydro-2H-indazol-5-ylmethyl)amino]carbonyl}pyrrolidinyl)ethylcarbamate using the proce-dure of EXAMPLE 8, and was obtained as a white crystalline solid.

Yield: 90% Melting point: 156–159° C. IR (KBr): ν3442, 2928, 1743, 1654, 1448, 1342, 1155, 754, 704 cm$^{-1}$.

EXAMPLE 66.

2-{[(1R)-1-(Cyclohexylmethyl)-2-oxo-2-((2S)-2-{[(4,5,6,7-tetrahydro-2H-indazol-5-ylmethyl)amino]carbonyl}pyrrolidinyl)ethyl]amino}acetic acid dihydrochloride

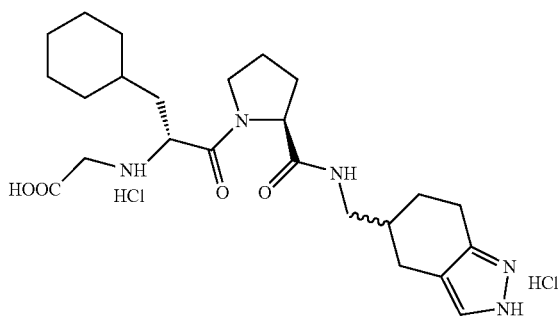

1. Preparation of tert-butyl 2-{[(tert-butoxycarbonyl)[(1R)-1-(cyclohexylmethyl)-2-oxo-2-((2S)-2-{[(4,5,6,7-tetrahydro-2H-indazol-5-ylmethyl)amino]carbonyl}pyrrolidinyl)ethyl]amino}acetate The title compound was prepared from (2S)-1-((2R)-2-{(tert-butoxycarbonyl)[2-(tert-butoxy)-2-oxoethyl]amino}-3-cyclohexylpropanoyl)-2-pyrolidinecarboxylic acid and 4,5,6,7-tetrahydro-2H-indazol-5-ylmethanamine dihydrochloride using the procedure of EXAMPLE 6, and was obtained as a white solid.

2. Preparation of 2-{[(1R)-1-(cyclohexylmethyl)-2oxo-2-((2S)-2-{[(4,5,6,7-tetrahydro-2H-indazol-5-ylmethyl)amino]carbonyl}pyrrolidinyl)ethyl]amino}acetic acid dihydrochloride The title compound was prepared from tert-butyl 2-{(tert-butoxycarbonyl)[(1R)-1-(cyclohexylmethyl)-2-oxo-2-((2S)-2-{[(4,5,6,7-tetrahydro-2H-indazol-5-ylmethyl)amino]carbonyl}pyrrolidinyl)ethyl]amino}acetate using the procedure of EXAMPLE 8, and was obtained as a white crystalline solid.

Yield: 91% Melting point: 144–147° C. IR (KBr): ν3424, 2924, 1738, 1652, 1554, 1446, 1236 cm$^{-1}$. MS (FAB): m/z 460 (%)(MH$^+$, 80).

EXAMPLE 67 tert-Butyl (1R)-2-[(2S)-2-({[(2-amino-5,6,7,8-tetrahydro-6-quinazolinyl)methyl]amino}carbonyl)pyrrolidinyl]-1-benzhydryl-2-oxoethylcarbamate

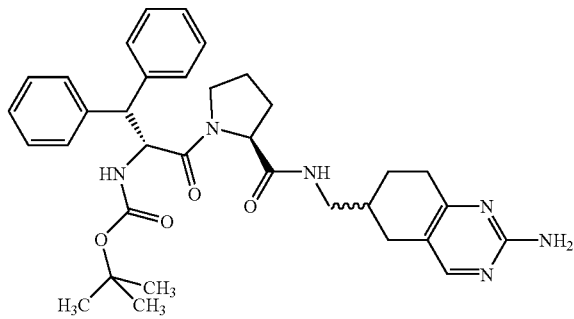

The title compound was prepared from Boc-D-3,3-(Ph)$_2$-Ala-L-Pro-OH and 6-(aminomethyl)-5,6,7,8-tetrahydro-2-quinazolinamine using the procedure of EXAMPLE 6, and was obtained as a white solid.

Yield: 44% Melting point: 127–130° C. IR (KBr): ν=3341, 2929, 1653, 1558, 1456, 1366, 1166, 1017, 755, 702 cm$^{-1}$. MS (EI): m/z 598 (%)(M, 51).

EXAMPLE 68

(2S)-1-[(2R)-2-Amino-3,3-diphenylpropanoyl]-N-[(2-amino-5,6,7,8-tetrahydro-6-quinazolinyl)methyl]-2-pyrrolidinecarboxamide dihydrochloride

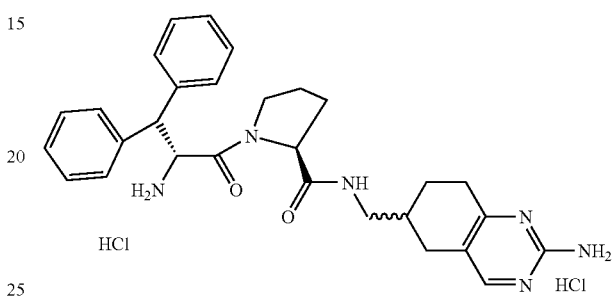

The title compound was prepared from tert-butyl (1R)-2-[(2S)-2-({[(2-amino-5,6,7,8-tetrahydro-6-quinazolinyl)methyl]amino}carbonyl)pyrrolidinyl]-1-benzhydryl-2-oxoethylcarbamate using the procedure of EXAMPLE 8, and was obtained as a white crystalline solid.

Yield: 98% Melting point: 166–168° C. IR (KBr): ν3305, 2926, 1654, 1449, 1357, 1188, 1004, 756, 704 cm$^{-1}$. MS (FAB): m/z 499 (%)(MH$^+$, 55).

EXAMPLE 69

(2S)-N-[(2-Amino-4,5,6,7-tetrahydro-1,3-benzothiazol-6-yl)methyl]-1-{(2R)-2-[(benzylsulfonyl)amino]-3-cyclohexylpropanoyl}-2-pyrrolidinecarboxamide

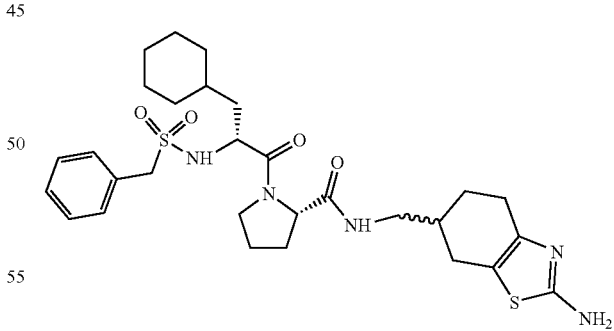

The title compound was prepared from N-(benzylsulfonyl)-D-(cyclohexyl-Ala)-L-Pro-OH and 4,5,6,7-tetrahydro-1,3-benzothiazole-2,6-diamine dihydrobromide according to the procedure of EXAMPLE 25, and was obtained as a faint yellow solid.

Yield: 77%. Melting point: 203–205° C. IR (KBr): ν=3356, 2924, 1648, 1523, 1444, 1311, 1141, 783, 699, 546 cm$^{-1}$. MS (FAB): m/z (%) 588 (MH$^+$, 100).

EXAMPLE 70 tert-Butyl 2-[[(1R)-2-((2S)-2-{[(2-amino-4,5,6,7-tetrahydro-1,3-benzothiazol-6-yl)amino]carbonyl}pyrrolidinyl)-1-(cyclohexylmethyl)-2-oxo-ethyl](tert-butoxycarbonyl)amino]acetate

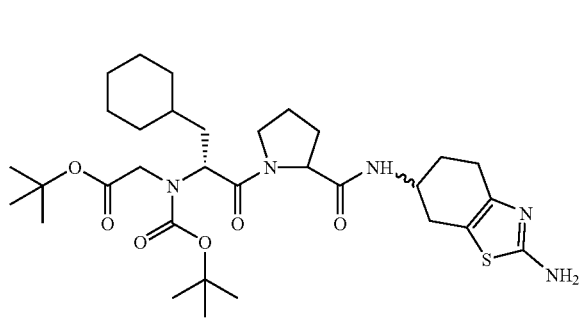

The title compound was prepared from (2S)-1-((2R)-2-{(tert-butoxycarbonyl)[2-(tert-butoxy)-2-oxoethyl]amino}-3-cyclohexylpropanoyl)-2-pyrrolidinecarboxylic acid and 4,5,6,7-tetrahydro-1,3-benzothiazole-2,6-diamine dihydrobromide according to the procedure of EXAMPLE 25, and was obtained as a white solid.

Yield: 65%. Melting point: 95–101° C. IR (KBr): ν=3318, 2978, 2927, 2852, 1750, 1698, 1646, 1529, 1447, 1368, 1228, 1158 cm$^{-1}$. MS (FAB): m/z (%) 634 (MH$^+$, 100).

EXAMPLE 71

2-{[(1R)-2-((2S)-2-{[(2-amino-4,5,6,7-tetrahydro-1,3-benzothiazol-6-yl)amino]carbonyl}pyrrolidinyl)-1-(cyclohexylmethyl)-2-oxoethyl]amino}acetic acid dihydrochloride

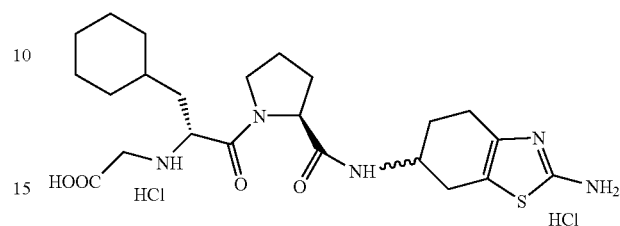

The title compound was prepared from tert-butyl 2-[[(1R)-2-((2S)-2-{[(2-amino-4,5,6,7-tetrahydro-1,3-benzothiazol-6-yl)amino]carbonyl}pyrrolidinyl)-1-(cyclohexylmethyl)-2-oxoethyl](tert-butoxycarbonyl)amino]acetate according to the procedure of EXAMPLE 26, as a white crystalline solid.

Yield: 91%. Melting point: 180–182° C. IR (KBr): ν=2929, 2288, 1742, 1639, 1548, 1448, 1227, 1116, 880, 710 cm$^{-1}$. MS (FAB): m/z (%) 478 (MH$^+$, 100).

EXAMPLE 72

Results of Biological Testing for Selected Compounds

| Structure | thrombin (μM) | trypsin (μM) | Ki trypsin/ Ki thrombin | aPTT (μM) | PT (μM) | TT (μM) |
|---|---|---|---|---|---|---|
| 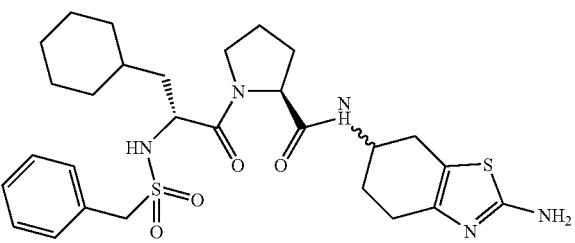 | 0.12 | >68.3 | >569 | 59 | 114 | 15 |
| 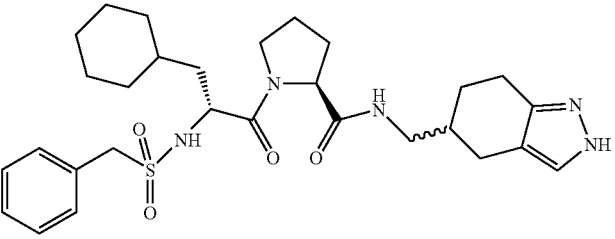 | 0.14 | 177.4 | 1267 | 42.3 | 78.3 | 11 |
| 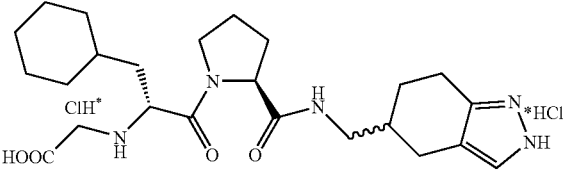 | 0.28 | 19.9 | 70.6 | 28 | 55.3 | 4.9 |

| Structure | thrombin (µM) | trypsin (µM) | Ki trypsin/ Ki thrombin | aPTT (µM) | PT (µM) | TT (µM) |
|---|---|---|---|---|---|---|
| 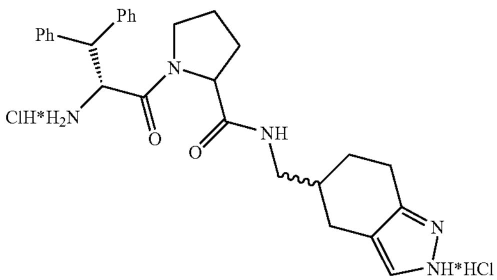 | 0.36 | 216.6 | 601.5 | 43 | 59.8 | 7.7 |
| 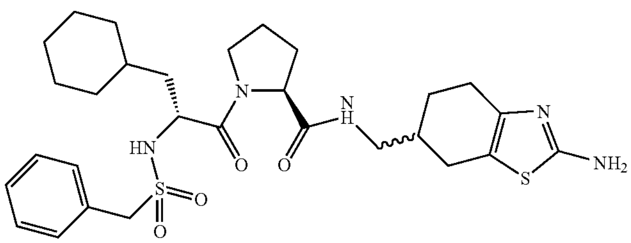 | 0.37 | 39.9 | 107.8 | 64 | 95.3 | 15.8 |
| 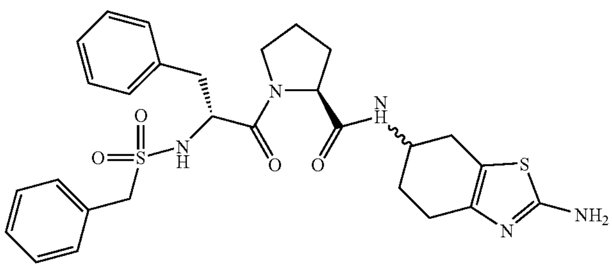 | 0.62 | >68.3 | >110 | 332 | 578 | 84 |

We claim:

1. Compounds of general formula (I)

D-CO—B-A-Het   (I)

wherein

Het represents a group selected from the group consisting of formulae:

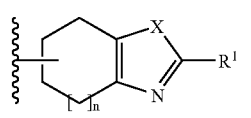

(1.4)

n = 0, 1
wherein X is S, NH or O,

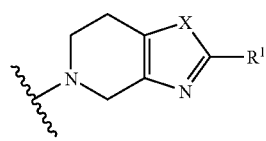

(1.8)

wherein X is NH, O or S, $R^1$ and $R^2$ independently represent H or $NH_2$;

A represents group —CONH— or —CH$_2$NH— attached to Het by the NH fragment, group —CONHCH$_2$— or —CH$_2$NHCH$_2$— attached to Het by the CH$_2$ fragment, group —CH$_2$NHCONH—, —CH$_2$NHCH$_2$CONH— or —CH$_2$NHCOCH$_2$NH— attached to Het by the NH fragment, group —CH$_2$NHCONHCH$_2$—, —CH$_2$NHCH$_2$CONHCH$_2$— or —CH$_2$NHCOCH$_2$NHCH$_2$— attached to Het by the CH$_2$ fragment;

B is selected from the group consisting of groups of formulae:

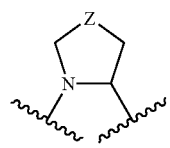

(2.1)

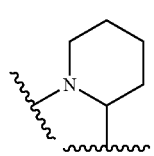

(2.2)

-continued (2.3)

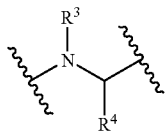

Z is CH$_2$, S or CH—OH
R$^3$ is H, straight or branched C$_1$–C$_4$ alkyl, C$_3$–C$_7$ cycloalkyl
R$^4$ is H, straight or branched C$_1$–C$_4$ alkyl, C$_3$–C$_7$ cycloalkyl;
D represents a group (3.0)

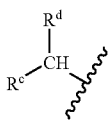

wherein R$^d$ is H, CH$_2$OH, CH$_2$SH or a group (3.0.1)

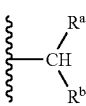

wherein
R$^a$ and R$^b$ are independently selected from the group consisting of:
H,
C$_1$–C$_4$ straight or branched alkyl which can be substituted with C$_3$–C$_7$ cycloalkyl or with 1 to 9 atoms of halogen selected from F, Cl, Br, I,
C$_3$–C$_7$ cycloalkyl,
C$_9$–C$_{10}$ bicycloalkyl,
a stable saturated or unsaturated 5- to 7-membrered monocyclic heterocyclic system, or a 8- to 10-membrered bicyclic heterocyclic system which, in addition to carbon atoms, contains 1 to 3 heteroatoms selected from the group consisting of N, O and S, in which N or S can be oxidized or N quaternized,
aryl which can be optionally unsubstituted or substituted at any position with one or two substituents selected from C$_{1-4}$ alkyl, C$_{1-4}$ alkoxy, halogen or hydroxy,
R$^c$ is selected from the group consisting of:
NH$_2$
NH(CH$_2$)$_n$CH$_3$, where n is 0, 1, 2 or 3,
NH(CH$_2$)$_m$OH, where m is 2, 3 or 4,
NH(CH$_2$)$_k$COOH, where k is 1, 2 or 3,
NH(CH$_2$)$_n$COOR$^5$, where n is 0, 1, 2 or 3 and R$^5$ represents C$_{1-4}$ straight or branched alkyl,
NH(CH$_2$)$_k$CONR$^6$R$^7$, where k is 1, 2 or 3 and R$^6$ in R$^7$ are independently H or straight or branched C$_{1-4}$ alkyl, or R$^6$ and R$^7$ together are —(CH$_2$)$_{4-5}$—, —(CH$_2$)$_2$O(CH$_2$)$_2$— or —(CH$_2$)$_2$NH(CH$_2$)$_2$—,
NHO$_2$S(CH$_2$)$_n$—W where n is 0, 1, 2 or 3,
W represents phenyl, naphthyl, a saturated or unsaturated monocyclic 5- or 6-membered or saturated or unsaturated bicyclic 8- to 10-membered heterocyclic ring which contains from 1 to 3 heteroatoms selected from the group consisting of N, O or S in which N or S can be oxidized or N quaternized; each ring may be optionally substituted by one or more substituents selected from the group consisting of C$_{1-4}$ alkyl, C$_{1-4}$ alkoxy, amino, cyano, halogen or hydroxy,
—N[O$_2$S(CH$_2$)$_n$—W][(CH$_2$)$_k$COOH]where n is 0, 1, 2 or 3 and where k is 1, 2 or 3,
NH(CH$_2$)$_k$NH$_2$, where k is 1, 2 or 3,
NHC(Ph)$_3$,
in the form of pure diastereomers or a mixture of diastereomers or pharmaceutically acceptable salts thereof with anticoagulant activity.

2. A compound as claimed in claim 1, of formula (1) wherein Het represents group.

3. A compound as claimed in preceding claim wherein A is selected from the group consisting of: —CONH— or —CH$_2$NH— attached to Het by the NH fragment, —CONHCH$_2$— or —CH$_2$NHCH$_2$— attached to Het by the CH$_2$ fragment.

4. A compound as claimed in claim 1, wherein B is selected from the group consisting of formulae numbers: 2.1. (Z is CH$_2$ or S), 2.2. or 2.3. (R$^3$ is H, C$_3$–C$_7$ cycloalkyl, R$^4$ is H or branched C$_1$–C$_4$ alkyl).

5. A compound as claimed in claim 1, wherein D represents a group selected from the group consisting of formula number 3.0. (wherein R$^d$ is H or 3.0.1 wherein R$^a$ may be phenyl, dichlorophenyl, 3,4-dichlorophenyl or cyclohexyl and R$^b$ is H, or wherein R$^a$ and R$^b$ are both phenyl or cyclohexyl).

6. A compound as claimed in claim 1, wherein said compound is selected from the group consisting of:
tert-Butyl (1R)-2-((2S)-2-{[(2-amino-4,5,6,7-tetrahydro-1,3-benzothiazol-6-yl)amino]carbonyl}pyrrolidinyl)-1-benzyl-2-oxoethylcarbamate;
(2S)-1-[(2R)-2-Amino-3-phenylpropanoyl]-N-(2-amino-4,5,6,7-tetrahydro-1,3-benzothiazol-6-yl)-2-pyrrolidinecarboxamide dihydrochloride;
(2S)-N-(2-amino-4,5,6,7-tetrahydro-1,3-benzothiazol-6-yl)-1-{(2R)-2-[(benzylsulfonyl)amino]-3-phenylpropanoyl}-2-pyrrolidinecarboxamide;
(2S)-N-(2-Amino-4,5,6,7-tetrahydro-1,3-benzothiazol-6-yl)-1-{(2R)-2-[(benzylsulfonyl)amino]-3-cyclohexylpropanoyl}-2-pyrrolidinecarboxamide;
(2S)-N-(2-Amino-4,5,6,7-tetrahydro-1,3-benzothiazol-6-yl)-1-[(2R)-2-[(benzylsulfonyl)amino]-3-(3,4-dichlorophenyl)propanoyl]-2-pyrrolidinecarboxamide;
(2S)-N-(2-Amino-4,5,6,7-tetrahydro-1,3-benzothiazol-6-yl)-1-{(2R)-2-[(2-naphthylsulfonyl)amino]-3-phenylpropanoyl}-2-pyrrolidinecarboxamide;
(2R)-N-{2-[(2-Amino-4,5,6,7-tetrahydro-1,3-benzothiazol-6-yl)amino]-2-oxoethyl}-2-[(benzylsulfonyl)amino]-3-phenylpropanamide;
(2R)-N-{(1S)-2-[(2-Amino-4,5,6,7-tetrahydro-1,3-benzothiazol-6-yl)amino]-1-methyl-2-oxoethyl}-2-[(benzylsulfonyl)amino]-3-phenylpropanamide;
(2S)-N-(2-Amino-4,5,6,7-tetrahydro-1,3-benzothiazol-6-yl)-1-[2-(tritylamino)acetyl]-2-pyrrolidinecarboxamide;
tert-Butyl (1R)-2-((2S)-2-{[(2-amino-4,5,6,7-tetrahydro-1,3-benzothiazol-6-yl)amino]carbonyl}pyrrolidinyl)-1-(3,4-dichlorobenzyl)-2-oxoethylcarbamate;
tert-Butyl (1S)-2-((2S)-2-{[(2-amino-4,5,6,7-tetrahydro-1,3-benzothiazol-6-yl)amino]carbonyl}pyrrolidinyl)-1-benzhydryl-2-oxoethylcarbamate;
(2S)-1-[(2R)-2-amino-3-(3,4-dichlorophenyl)propanoyl]-N-(2-amino-4,5,6,7-tetrahydro-1,3-benzothiazol-6-yl)-2-pyrrolidinecarboxamide dihydrochloride;

(2S)-1-[(2S)-2-amino-3,3-diphenylpropanoyl]-N-(2-amino-4,5,6,7-tetrahydro-1,3-benzothiazol-6-yl)-2-pyrrolidinecarboxamide dihydrochloride;

(2S)-N-[(2-Amino-4,5,6,7-tetrahydro-1,3-benzothiazol-6-yl)methyl]-1-{(2R)-2-[(benzylsulfonyl)amino]-3-cyclohexylpropanoyl}-2-pyrrolidinecarboxamide;

tert-Butyl 2-[[(1R)-2-((2S)-2-{[(2-amino-4,5,6,7-tetrahydro-1,3-benzothiazol-6-yl)amino]carbonyl}pyrrolidinyl)-1-(cyclohexylmethyl)-2-oxoethyl](tert-butoxycarbonyl)amino]acetate; and 2-{[(1R)-2-((2S)-2-{[(2-amino-4,5,6,7-tetrahydro-1,3-benzothiazol-6-yl)amino]carbonyl}pyrrolidinyl)-1-cyclohexylmethyl)-2-oxoethyl]amino}acetic acid dihydrochloride.

7. A compound of inhibiting coagulation comprising administering an effective amount of a compound as claimed in claim 1.

8. A process for the preparation of compounds as claimed in any of claims 1 to 6, characterized in that A is selected from the group consisting of:

—CONH— attached to Het by the —NH— fragment or A is group —CONHCH$_2$— attached to Het by the —CH$_2$— fragment, fragment B having protecting group or D-CO fragment attached to N-atom and COOH group attached to C-atom adjacent to nitrogen is condensed with Het-NH$_2$ or Het-CH$_2$NH$_2$ compound, and when a protecting group is attached to N of fragment B, after condensation it is removed, and the obtained fragment is condensed with a D-COOH group;

—CH$_2$NH— attached to Het by the —NH— fragment or group —CH$_2$NHCH$_2$— attached to Het by the —CH$_2$— fragment, by reductive amination of aldehydes B—CHO bearing a suitable protecting group P attached to N, with Het-NH$_2$ or HetCH$_2$NH$_2$ amines, P—B—CH$_2$NH-Het fragment or P—B—CH$_2$NHCH$_2$-Het fragment is prepared and after removal of protecting group P the obtained compound is condensed with D-COOH fragment;

—CH$_2$NHCONH— attached to Het by the —NH— fragment, from aldehyde B—CHO, in which a suitable protecting group P is attached to N, which is introduced and on completed reaction removed, by reductive amination with ammonium acetate and subsequent conversion of obtained amine with ethyl chloroformate a compound of the type P—B—CH$_2$NHCOOEt is obtained which is condensed with Het-NH$_2$ and then after deprotection B—CH$_2$NHCOHN-Het fragment is condensed with the D-COOH;

—CH$_2$NHCONHCH$_2$— attached to Het by the —CH$_2$— fragment, from aldehyde B—CHO, wherein a suitable protecting group P is attached to N, by reductive amination with ammonium acetate and subsequent conversion of the obtained amine with ethyl chloroformate a compound of the type P—B—CH$_2$NHCOOEt is obtained which is condensed with Het-CH$_2$NH$_2$ and then after deprotection, B—CH$_2$NHCOHNCH$_2$-Het fragment is condensed with the D-COOH;

—CH$_2$NHCH$_2$CONH— attached to Het with —NH— fragment from aldehyde B—CHO, wherein a suitable protecting group P is attached to N, by reductive amination with ammonium acetate and subsequent conversion of obtained amine with ethyl bromoacetate a compound of the type P—B—CH$_2$NHCH$_2$COOEt is obtained which is condensed with Het-NH$_2$ and then after deprotection, the B—CH$_2$NHCOHN-Het fragment is condensed with the D-COOH fragment;

—CH$_2$NHCH$_2$CONHCH$_2$— attached to Het by the —CONHCH$_2$— fragment, from aldehyde B—CHO, wherein a suitable protecting group P is bound at N, by reductive amination with ammonium acetate and subsequent conversion of the obtained amine with ethyl bromoacetate a compound of the type P—B—CH$_2$NHCH$_2$COOEt is obtained which is condensed with Het-CH$_2$NH$_2$ and then after deprotection, B—CH$_2$NHCH$_2$COHNCH$_2$-Het fragment is condensed with the D-COOH fragment;

—CH$_2$NHCOCH$_2$NH— attached to Het by the —NH— fragment, the reaction between Het-NH$_2$ and ethyl bromoacetate is carried out, the obtained HetNHCH$_2$COOEt compound then converted to B—CH$_2$NHCOCH$_2$NHHet compound using B—CH$_2$NH$_2$ compound; and —CH$_2$NHCOCH$_2$NHCH$_2$— attached to Het by the —CH$_2$NHCH$_2$— fragment, the reaction between Het-CH$_2$NH$_2$ and ethyl bromoacetate is carried out, and the HetCH$_2$NHCH$_2$COOEt compound is converted to B—CH$_2$NHCOCH$_2$NHCH$_2$Het using B—CH$_2$NH$_2$ compound, and then the B—CH$_2$NHCOCH$_2$HNCH$_2$-Het fragment is condensed with the D-COOH fragment.

9. A method for inhibiting thrombin, inhibiting formation of fibrin, and for inhibiting thrombus formation comprising administering an effective amount of a compound as claimed in claim 1.

10. A method for inhibiting a condition selected from the group consisting of venous thrombosis, pulmonary embolisms in heart patients, blood coagulation in extracorporeal circuits and hemodialysis, the method comprising administering an effective amount of a compound as claimed in claim 1.

11. A pharmaceutical composition comprising a therapeutically effective amount of a compound of any of claims 1 to and pharmaceutically acceptable auxiliary substances.

12. A method for inhibiting thrombin in man and other mammals comprising administering a compound as claimed in any of claims 1.

13. A method for inhibiting formation of fibrin and thrombus formation in man and other mammals comprising administering a therapeutically effective amount of a compound of claims 1.

14. A compound according to claim 1, wherein $R^a$ or $R^b$ is an aryl moiety selected from the group consisting of phenyl and naphthyl.

* * * * *

UNITED STATES PATENT AND TRADEMARK OFFICE
CERTIFICATE OF CORRECTION

PATENT NO. : 7,112,590 B2
APPLICATION NO. : 10/275215
DATED : September 26, 2006
INVENTOR(S) : Danijel Kikelj et al.

It is certified that error appears in the above-identified patent and that said Letters Patent is hereby corrected as shown below:

Col. 59, line 9 claim 1
add --wherein:--

Col. 59, line 37 claim 1
replace "selected from"
with --selected from the the group consisting of:--

Col. 59, line 41 claim 1
replace "membrered"
with --membered--

Col. 59, line 42-43 claim 1
replace "membrered"
with --membered--

Col. 60, line 14 claim 2
replace "group"
with --group 1.4--

Col. 60, line 15 claim 3
replace "preceding claim"
with --claim 1--

Col. 61, line 15 claim 7
replace "compound"
with --method--

Col. 62, line 45 claim 8
replace "of any of claims 1 to"
with --according to claim 1--

Signed and Sealed this

Thirteenth Day of July, 2010

David J. Kappos
*Director of the United States Patent and Trademark Office*

CERTIFICATE OF CORRECTION (continued)
U.S. Pat. No. 7,112,590 B2

Col. 62, line 49 claim 12
replace "any of claims"
with --claim--

Col. 62, line 53 claim 13
replace "claims"
with --claim--